US006350368B1

United States Patent
Willner et al.

(10) Patent No.: US 6,350,368 B1
(45) Date of Patent: Feb. 26, 2002

(54) ELECTROCHEMICAL AND PHOTOCHEMICAL ELECTRODES AND THEIR USE

(75) Inventors: Itamar Willner, Mevasseret Zion; Eugeny Katz, Jerusalem; Ron Blonder, Jerusalem; Vered Heleg-Shabtai, Jerusalem, all of (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/194,364

(22) PCT Filed: May 27, 1997

(86) PCT No.: PCT/IL97/00169

§ 371 Date: Jun. 30, 1999

§ 102(e) Date: Jun. 30, 1999

(87) PCT Pub. No.: WO97/45720

PCT Pub. Date: Dec. 4, 1997

(30) Foreign Application Priority Data

May 27, 1996 (IL) .................................. 118432

(51) Int. Cl.[7] .......................... G01N 27/26; B01D 1/00; G11B 7/00
(52) U.S. Cl. ................... 205/777.5; 204/403; 427/2.13; 427/58; 369/121
(58) Field of Search ........................ 204/403; 435/817; 369/126, 120, 121; 427/2.1, 2.11, 2.13, 58; 205/777.5

(56) References Cited

U.S. PATENT DOCUMENTS 4,704,193 A * 11/1987 Bowers et al. ........... 205/777.5

4,797,181 A   1/1989 Durfor et al.
5,443,701 A   8/1995 Willner et al.

FOREIGN PATENT DOCUMENTS

DE   4118880 A1 * 12/1992

OTHER PUBLICATIONS

EP abstract of DE 4118880A1 (Otto et al.), Dec. 1992.*

Massey, V., et al., "Artificial Flavins as Active Site Probes of Flavoproteins," in "Flavins and Flavoproteins," Elsevier, Amsterdam 83–96 (1982) month unknown.

Ritlin, A., et al., "Improving Enzyme–Electrode Contacts by Redox Modification of Cofactors," *Letters to Nature* 376:672–675 (Aug. 1995).

(List continued on next page.)

*Primary Examiner*—T. Tung
*Assistant Examiner*—Alex Noguerola
(74) *Attorney, Agent, or Firm*—Browdy and Neimark

(57) ABSTRACT

Electrodes carrying FAD-dependent enzymes on their surface are enclosed. The FAD is modified to include a functional group or moiety which affects the properties of the enzyme. The functional group or moiety can be a binding moiety through which the FAD-enzyme complex is immobilized onto the electrode; it can be an electron mediator group for transferring electrons between the electrode and the FAD; or it can be a photoisomerizable group which can undergo photoisomerization which yields a change in the rate of the electrically induced catalytic activity of the enzyme. The electrodes can be used in electrochemical systems for deforming analytes in liquid medium or for recordal of optical signals.

14 Claims, 21 Drawing Sheets

OTHER PUBLICATIONS

Willner, I., et al., "Reconstitution of Apo–Glucose Oxidase with a Nitrospyr₀pyran–Modified FAD Cofactor Yields a Photoswitchable Biocatalyst for Amperometric Transduction of Recorded Optical Signals," *J. Am. Chem. Soc.* 118:5310–5311 (1996) month unknown.

Willner, I., et al., "Photoswitchable Biomaterials as Grounds for Optobioelectronic Devices," *Bioelectrochemistry and Bioenergetics* 42:43–57 (1997) month unknown.

Abstract of SU 593,439, (1980) month unknown.

Abstract of Janpanese Patent 62 115284, May 1987.

Willner, I., et al., "Development of Novel Biosensor Enzyme Electrodes: Glucose Oxidase Multilayer Arrays Immobilized onto Self–Assembled Monolayers on Electrodes," *Advanced Materials* 5–12:912–915 (1993) month unknown.

Willner, I., et al., "Control of the Structure and Functions of Biomaterials by Light," *Angew. Chem. Int. Ed. Engl.* 35:367–385 (1996) month unknown.

Willner, I., et al., "Bioelectrocatalyzed Amperometric Transduction of Recorded Optical Signals Using Monolayer–Modified Au–Electrodes," *Journal of American Chemical Society* 117:6581–6592 (1995) month unknown.

Lion–Dagan, M., et al., "Amperometric Transduction of Optical Signals Recorded by Organized Monolayers of Photoisomerizable Biomaterials on Au Factors," *Journal of American Chemical Society* 116:7913–7914 (1994) month unknown.

Willner, I., et al., "Mediated Electron Transfer in Glutathione Reductase Organized in Self–Assembled Monolayers on Au Electrodes," *Journal of American Chemical Society* 114:10965–10966 (1992) month unknown.

Degani, Y., et al., "Direct Electrical Communication between Chemically Modified Enzymes and Metal Electrodes 2. Methods for Bonding Electron–Transfer Relays to Glucose Oxidase and D–Amino–Acid Oxidase," *Journal of American Chemical Society* 110:2615–2620 (1988) month unknown.

Katz, E., et al., "Electrochemical Study of Pyrroloquinoline Quinone Covalently Immobilized as a Monolayer Onto a Cystamine–Modified Gold Electrode," *Journal of Electroanalytical Chemistry* 367:59–70 (1994) month unknown.

Namba, K., et al., "Normal and Reverse Photochromism of 1–(β–carboxyethyl)–3,3–dimethyl–6'–nitrospiro [indoline–2,2'–2H–benzopyran] in Water–Dioxane," *Bull. Chem. Soc. Jpn.* 48:1323–1324 (1975) month unknown.

Walsh, C., et al., "Chemical and Enzymatic Properties of Riboflavin Analogues," *Biochemistry* 78:1942–1951 (1978) vol. 10, 1978 month unknown.

Buckmann, A.F., et al., "N[6]–(2–Aminoethyl)–FAD: Synthesis and Coenzyme Activity with Respect to Apo–NADH Oxidase from Thermus Termophilus and Termus Aquaticus," in "Flavins and Flavoproteins," Gruyter, Berlin: 597–602 (1994) month unknown.

* cited by examiner

EDC,NHS
HEPES 0.1M, pH=7.4

(PQQ)

ELECTROCHEMICAL AND PHOTOCHEMICAL ELECTRODES AND THEIR USE

FIELD OF THE INVENTION

The present invention is generally in the field of bioelectronics and concerns electrically conducting solid matrices (to be referred to herein as "electrodes") carrying redox enzymes such that an electric charge can flow between the surface of the electrode and the enzymes rendering them catalytically active. Also provided by the invention is a process for the preparation of the electrodes as well as devices, systems and methods making use of such electrodes. In accordance with one embodiment, the invention is applied for the determination of the presence and optionally the concentration of an analyte in a liquid medium. In accordance with another embodiment, the immobilized enzymes can be switched by light into two distinct biocatalytic states thus allowing the transduction and amplification of recorded optical signals thus fulfilling "read" and "write" functions, rendering such electrodes useful in optical information storage and processing.

PRIOR ART

The prior art believed to be relevant as a background to the present invention consists of the following:
1. Degani, Y., Heller, A., *J. Am. Chem. Soc.*, 110:2615, 1988.
2. Willner, I., Katz, E., Riklin, A., Kasher R., *J. Am. Chem. Soc.*, 114:10965, 1992.
3. Willner et al., U.S. Pat. No. 5,443,701.
4. Lion-Dagan, M . Katz, E., Willner, I., *J. Amer. Chem. Soc.*, 116791 3, 1994.
5. Willner, I., Lion-Dagan, M., Marx-Tibbon, S., Katz, E., *J. Amer. Chem. Soc.*, 117:6581, 1995.
6. Willner, I. and Rubin, S., *Angen. Chem. Int. Ed.* Engl. 35: 367 , 1996.
7. Willner, I., Riklin, A., Shoham, B., Rivenson, D., Katz, E., *Adv. Mater.*, 5:912, 1993.
8. Massey, V., Hemmerich, P., in *Flavins and Flavoproteins*, V. Massey & C. H. Williams (Eds.), Elsevier, Amsterdam, 83–96, 1982.
9. Walsh, C., Fisher, J., Spencer, R., Graham, D. W., Ashton, W. T., Brown, J. E., Brown, R. D., Rogers, E. F., *Biochemistry*, 78:1942, 1978.
10. Buckmann, A. F., Erdmann, H., Pietzch, M., Hall, J. M., Bannister, J. V. in K. Kuneoyagi (Ed.), Flavins and Flavoproteins, Gruyter, Berlin, p. 597, 1994.
11. Riklin, A., Katz, E., Willner, I., Stocker, A., Buckmann, A.F., *Nature*, 376:672, 1995.
12. Willner, I., Liondagan, M., Marxtibbon S., Katz, E., *J. Amer. Chem. Soc.*, 117: 6581, 1995
13. Namba, K., Suzuki, S., *Bull. Chem. Soc. Jpn.*, 48:1323, 1975.
14. Katz, E., Schlereth, D. D., Schmidt, H. L., *J. Electroanal. Chem.*, 367:59, 1994.

BACKGROUND OF THE INVENTION

Covalent coupling of redox active groups (ferrocene, bipyridinium, etc.) to amino acid residues of redox enzymes produces biocatalysts that electrically communicate with electrodes electrically "wired" enzymes[1–3]. Enzymes modified by photoisomerizable groups (e.g. nitrospiropyran/nitromerocyanine) show different enzymatic activities for the different light-induced generated photoisomer states[4,5]. The use of photoswitchable biocatalysts as active matrices for optical recordings and optobioelectric devices was recently reviewed[6].

Electrically-wired enzymes were employed for the determination of analytes in electrochemical cells by the attachment of the electrobiocatalyse to electrodes[3,7]. In all of the described systems, the functional electroactive or photoactive units are randomly distributed around the protein. The effectiveness of electrical contact between the enzyme redox-center and the electrode is limited. As a result, the rate of electron transfer between the enzyme redox center is relatively slow. This results in competitive electron transfer reactions with co-substrates (e.g. oxygen) or interfering substrates (e.g. oxidation of uric acid or ascorbic acid). As a result the magnitude of the resulting currents that assay the respective analytes are moderately low and the analysis had to be performed in an oxygen free environment. Special care had to be made to eliminate any interfering reagents from the analysis medium.

For many enzymes (e.g. flavoenzymes) the FAD-cofactor can be removed from the native protein to yield the unfolded apo-protein which can be reconstituted back with the natural cofactor or chemically modified FAD cofactors to yield the bioactive enzyme[8–10]. The reconstitution of apo-flavoenzymes with a FAD-cofactor bound to an electron mediator group generated an "electro enzynze" that exhibited electrical contact with electrode surfaces. Mediated electron transfer activates the reconstituted enzymes for the electrocatalytic oxidation of their substrates[11].

Enzyme-electrodes for electrochemical determination of an analyte can operate as non-invasive or invasive analytical devices. For invasive analyses the electrodes must be constructed of bio compatible non-hazardous substances, and the electrodes must be fabricated as thin needles to exclude pain upon invasive penetration. The low surface area of the electrodes must be compensated by a high electrical activity of the sensing biocatalysts to yield measurable current responses.

The functions of enzymes modified by randomly substituted photoisomerizable units are only incompletely switched by external light signals. The perturbation structure of the protein environment of the active redox center of enzymes is only partially affected by remote photoisomerizable units. This yields only to partial, incomplete, deactivation of the photoisomerizable enzyme[12].

GENERAL DESCRIPTION OF THE INVENTION

It is an object of the present invention to provide an electrochemical method and system for the determination of the presence and optionally the concentration of an analyte in a liquid medium.

It is furthermore an object of the invention to provide electrodes for use in such method and system. It is particularly an object of the invention to provide such electrodes comprising a solid, electrically conducting matrix carrying immobilized enzymes such that electric charge and flow between the electrode to the enzymes renders the enzyme catalytically active whereby they catalyze a reaction in which the analyte to be assayed is converted into a product.

It is furthermore an object of the invention to provide such electrodes with high and efficient electron transport between the electrode and the enzymes such that the electrode is essentially insensitive to the presence of otherwise interfering redox reagents, i.e. there is a minimum of non-specific redox reactions.

It is furthermore an object of the invention to provide enzyme-electrodes where the entities immobilized on the electrodes are non toxic and non immunogenic enabling the use of the electrode in invasive analysis.

It is furthermore an object of the invention to provide enzyme-electrodes with photoswitchable enzymes immobilized on the electrode surface, for use in the recordal of optical signals and transduction of recorded optical signals.

It is another object of the invention to provide uses of the electrodes of the invention as well as processes for their preparations.

Other objects of the invention will be clarified from the description below.

The present invention has two aspects: one aspect, to be referred to herein as the "first aspect" in which the electrode is useful for the determination of the presence and optionally the concentration of an analyte in a liquid medium; and another aspect, to be referred to herein as the "second aspect", in which the electrical response of the electrode is photoregulated (i.e. the degree of electrical response is controllable by irradiation of light at a specific wavelength) allowing the use of the electrode in recordal of optical signals and the electrical transduction of recorded optical signals. Both aspects of the present invention share a common denominator in that the electrodes carry immobilized enzymes, and in that the enzymes have functionalized cofactors, i.e., cofactors modified by the addition of a functional group or moiety (such enzymes to be referred to at times as "functionalized enzymzes").

In accordance with the invention a functionalized enzyme may be obtained by reconstituting an apo-enzyme (an enzyme without its cofactor) with a FAD modified by the addition of a functional group or moiety ("functionalized FAD").

In accordance with one embodiment the functional group or moiety is a binding moiety capable of chemical association with, attachment to or being chemically sorbed onto the surface of the electrode. In accordance with another embodiment, the functional group or moiety is an electron mediator group which is a group capable of reversibly changing its redox state and transfer electrons to and from the FAD. In accordance with a further embodiment the functionalized group is a photoisomerizable group which can change its isomerization state upon photostimulation. It is possible also in accordance with other embodiments of the invention for the functionalized FAD to have more than one functional group or moiety, e.g. a binding moiety and an electron mediator group, or a binding moiety and a photoisomerizable group, etc.

In the case of a functionalized FAD having an electron mediator group, and particularly such wherein the functionalized FAD has both a binding moiety and an electron mediator group, there is a highly efficient electron transfer between the electrode and the FAD, yielding enzyme turnover rate which approaches maximal theoretical considerations. Such an electrode which is useful particularly in accordance with the first aspect of the invention, gives rise to a very high electrical response to a change in analyte concentration. Furthermore, the high turnover rate renders the electrode essentially insensitive to interfering agents such as non-specifically oxidizing or reducing agents, e.g. oxygen, ascorbic acid, uric acid, etc.

In accordance with the first aspect of the invention, the functionalized FAD preferably comprises an electron mediator group. It should be noted that where the functionalized FAD in the functionalized enzyme used in the first aspect does not comprise an electron mediator group, there is an electron mediator group which may be freely tumbling in solution or independently immobilized on the surface of the electrode, side by side with the modified FAD.

In accordance with the second aspect of the invention, wherein the functionalized FAD has a photoisomerizable group, enzymes have two catalytic states representing "ON" and "OFF" states. This allows the "writing" of a photo event on the surface of the electrode which is then "memorized" by the electrode by means of the induced photoisomerizable state of the functionalized cofactor, and this state can then be "read" by the electrode by measuring a change in the electrical response.

In the method and system of the invention, the changes in the analyte's concentration in the case of the first aspect or a change in the photoisomerization state in the case of the second aspect gives rise to a change in the electrical response. The term "electrical response" which is used herein denotes the current-voltage behavior of an electrode, e.g. the current response or the flow of charge of an electrode under a certain applied potential, etc. The electrical response may be determined by measuring current or charge flow, under alternating current or direct current conditions.

In the following the term "determine" or "determination" will be used to denote both determination of only the presence or determination of both the presence and concentration of an analyte in a liquid medium.

In the following, use will also be made of the term "reconstitution" referring to the joining together of an apo-enzyme (enzyme without its cofactor) with a cofactor to obtain a functionalized enzyme. In accordance with the invention the reconstitution of the enzyme is performed with a synthetic, functionalized FAD-cofactor. The term "reconstituted functionalized enzyme" will be used to denote an enzyme obtained by reconstitution of an apo-enzyme with a functionalized cofactor.

The functionalized enzyme reconstituted with a functionalized FAD will have properties which will be influenced by the type of the FAD modification. For example, a functionalized enzyme having a FAD comprising a linking group with a binding moiety and having an electron mediator group will be electrobiocatalytically active and capable of directly receiving electrons from or transferring electrons to the electrode (depending on whether it catalyzes in a reduction or oxidation pathway, respectively), without the need for a separate electron mediator group. Such a functionalized enzyme exhibits a highly efficient electrical contact with the electrode with an enzyme turnover approaching maximal theoretical consideration. A functionalized enzyme with a functionalized FAD having a photoisomerizable group will have different electrobiocatalytic properties, depending on the isomerization state of the photoisomerizable group; the catalytic properties of the enzyme can thus be controlled by light.

In accordance with the teaching of the invention there is thus provided an electrode carrying FAD-dependent enzymes on its surface, the enzymes having a functionalized FAD, being an FAD modified by the addition of a functional group or moiety, being one or more of the group consisting of:

(a) a binding moiety which can chemically associate with, attach to or chemically sorb onto the electrode, the enzyme being immobilized on the electrode by binding of the binding group to the electrode's surface;

(b) an electron mediator group which can transfer electrons between the surface of the electrode and the FAD; and (c) a photoisomerizable group which can change from one isomerization state to another by exposure to light of a first wavelength, such photoisomerization either increases or decreases the electrically induced catalytic activity.

Preferred electrodes for use in accordance with the first aspect of the invention are such wherein the functionalized FAD comprises both a binding moiety and an electron mediator group. Typically the electron mediator group will be sandwiched between the binding moiety and the remainder of the functionalized FAD thus allowing efficient and rapid electron transfer between the surface of the electrode and the FAD.

In electrodes for use in accordance with the second aspect of the invention the functionalized enzymes may at times be bound to the electrode by means of a group linked to a surface residue of the protein at its one end and having a binding moiety at its other end. Alternatively, the functionalized FAD may comprise both a photoisomerizable group and a binding moiety bound to the electrode.

The present invention also provides a process for preparing an electrode having FAD-dependent redox enzymes immobilized thereon, the process comprising:

(a) preparing apo-enzymes by treating an FAD-dependent enzyme so as to remove the FAD-cofactor therefrom;

(b) preparing a functionalized FAD by covalent binding to a binding moiety capable of chemical association with, attachment to or a chemical sorption to the surface of the electrode;

(c) reacting the functionalized FAD with the electrode under conditions such that the modified FAD becomes immobilized onto the electrode through chemical association, attachment or sorption of the binding moiety onto the surface of the electrode; and (d) reacting the electrode obtained in (c) with the apo-enzyme under conditions in which the apo-enzyme combines with the modified FAD to yield functional immobilized enzymes.

As will be appreciated, in the above process, steps (a) and (b) can be reversed. Furthermore, it is at times possible to first combine the apo-enzyme with the modified FAD and only then immobilizing the entire complex onto the surface of the electrode.

Where the functionalized FAD comprises other functional groups, i.e. an electron mediator group or a photoisomerizable group, these may be, a priori, included in the modified FAD prior to its immobilization onto the electrode, or may be added to the modified FAD after immobilization. A preferred immobilization scheme for preparing an electrode for use in accordance with the first aspect, comprises:

(a) treating an electrode to obtain a monolayer comprising an electron mediator group, the electron mediator group having a binding moiety which is capable of chemical association with, attachment to or chemical sorption to the surface of the electrode, the treatment comprising binding of the binding moiety onto the surface of the electrode;

(b) reacting the electrode obtained in (a) with an FAD such that the FAD becomes immobilized onto the electrode through chemical attachment to the electron mediator group;

(c) reacting the electrode obtained in (b) with apo-enzyme under conditions in which the apo-enzyme combines with the FAD component of the modified FAD.

The present invention further provides, by another of its facets, an electrochemical system for determining the presence of an analyte liquid medium, the system comprising:

(a) an electrode carrying on its surface FAD-dependent enzymes, the enzymes being capable of catalyzing a redox reaction in which an analyte is converted into a product, the enzymes comprising a functionalized FAD having a binding moiety which is chemically associated with, attached to or chemically sorbed onto the surface of the electrode;

(b) an electron mediator group which can transfer electrodes between the surface of the electrode and the FAD, the electron mediator group either
   (ba) forming part of or being covalently bound to the functionalized FAD,
   (bb) being independently immobilized onto the surface of the electrode,
   (bc) being covalently bound to the enzyme, or
   (bd) being freely tumbling (i.e. being non immobilized) in a medium surrounding the electrode; and (c) an electrical circuitry for charging the electrode and measuring the electrical response.

As will be appreciated, the analyte specificity of the system is determined by the type of the immobilized enzyme.

The present invention further provides a method for determining the presence of an analyte in a liquid medium, the method comprising:

(a) providing an electrochemical system as defined above;

(b) introducing a sample of said liquid medium into the electrochemical cell of the system;

(c) charging the electrode and measuring the electrical response, a change in the electrical response as compared to an electrical response under the same condition in a control medium which does not comprise the analyte, indicating the presence of the analyte in the system.

Electrodes in accordance with the first aspect of the invention exhibit high turnover rates which approaches theoretical concentrations and are thus essentially insensitive to various non-specific oxidizing or reducing agents such as oxygen, etc. This is particularly the case in electrodes of the invention where the electron mediator group forms part of or is covalently attached to the functionalized FAD. Such electrodes are thus suitable for performing measurement in a non protected environment. e.g., measurement performed in vivo. A particular example is an electrode in the form of a needle which can be inserted into a blood vein and continuously measure a desired parameter, e.g. glucose level. All the entities of the surface of the electrodes, i.e. the enzymes, may be made to be identical to such normally present within the body and accordingly there will typically be no immune response or any toxic effect, which may otherwise result from a continuous exposure to a foreign entity.

Electrodes and systems for continuous in vivo measurement of various parameters, are particularly preferred in accordance with the first aspect of the invention.

Enzymes which can be used in accordance with the invention include glucose oxidase (GOD), in which case the analyte will be glucose; D-aminoacid oxidase (DAAO), in which case the analyte is a D-aminoacid (e.g. D-alanine); lactate oxidase (LacOx), in which case the analyte is lactic acid; glutathione reductase (GR), in which case the analyte is oxidized glutathione; and many other flavoenzymes.

In accordance with a second aspect of the invention there is provided an electro chemical 'system for the recordal of optical signals having a first wavelength and the electrical transduction of the recorded signals, the system having an electrochemical cell comprising:

(a) an electrode carrying immobilized FAD-dependent redox enzymes, the enzyme:
   (aa) having a functionalized FAD comprising a photoisomerizable group which changes its isomerization state from a first to a second state upon photostimulation of light of the first wavelength, a change in the isomerization state giving rise to a change in the rate of catalytic activity of the redox enzyme,
(ab) being immobilized onto the surface of the electrode through a linking group which either
(aba) forms part of or being covalently bound to the functionalized FAD, or
(abb) is covalently bound to an external moiety on the surface of the enzyme;
(b) an electron mediator group which can transfer electrons between the electrode and the FAD, the electron mediator group being either
(ba) freely tumbling in the medium surrounding the electrode,
(bb) independently immobilized onto the surface of the electrode,
(bc) covalently bound to the enzyme, or
(bd) covalently bound to or forming part of the modified FAD;
(c) a substrate for the catalytic activity of the enzyme; and
(d) an electric circuitry for charging the electrode and measuring the electrical response.

Preferably, the photoisomerizable group can be isomerized reversibly by exposure to light to different wavelength regions. Thus, light irradiation at a first wavelength will change the isomerization state from a first state to a second state whereas light of a second wavelength will change the isomerization state between the second state to the first state. Accordingly, the system may comprise a light source irradiating light at the second wavelength for changing the isomerization state from the second back to the first state. Thus, the system will record light events at a first wavelength and can then be reset by the second wavelength emitted from the system's light source.

The present invention further provides, in accordance with the second aspect, a method for recordal of optical signals having a first wavelength and electrical transduction of the recorded optical signals, the method comprising:
(a) providing an electro chemical system as defined above;
(b) exposing the electrode to a light source;
(c) charging the electrode and measuring the electrical response, changing the electrical response indicating exposure to light having said first wavelength.

The present invention still further provides a process for preparing electrodes for use in accordance with the second aspect of the invention, the process comprising:
(a) preparing apo-enzyme by treating a FAD-dependent enzyme so as to remove the FAD therefrom;
(b) preparing a modified FAD by covalent binding of a group capable of attachment or binding to a photoisomerizable group;
(c) reacting the modified FAD with the photoisomerizable group to yield a photoisomerizable FAD;
(d) combining the apo-enzyme with the photoisomerizable FAD to yield a reconstituted photoisomerizable redox enzyme; and
(e) providing an electrode carrying linking groups immobilized thereon and reacting the reconstituted enzymes with the electrodes such that the enzymes become covalently bound to the linking group.

Another process to prepare an electrode in accordance with a second aspect, comprises:
(a) preparing apo-enzyme by treating a FAD-dependent enzyme so as to remove the FAD therefrom;
(b) preparing a modified FAD by covalent binding of a group capable of attachment or binding to a photoisomerizable group;
(c) reacting the electrode with a linking group having a binding moiety capable of association, chemical binding or sorption to the electrode and having a functional unit capable of binding to a photoisomerizable group, the reaction being under condition so that said binding moiety associates, chemically binds or sorbs with the surface of the electrode;
(d) reacting the electrode obtained in (c) with a photoisomerizable group;
(e) reacting the electrode obtained in (d) with the modified FAD obtained in (b), such as to obtain a monolayer comprising immobilized photoisomerizable FAD moieties on the electrode; and
(f) reacting the apo-enzymes with the electrode obtained in (e) under condition whereby the enzyme is reconstituted on the surface of the electrode thus yielding photo active redox enzymes immobilized on the electrode.

Enzymes which can be used in accordance with the second aspect of the invention include those mentioned above in connection with the first aspect.

A linking group which can be utilized in accordance with the present invention to immobilize an FAD onto the surface of an electrode, may have the following general formula (I):

$$Z-R^1-Q \qquad (I)$$

wherein:

Z is a binding moiety in case where the electrode is made of gold, platinum or silver, represents a sulphur-containing moiety which is capable of chemical association with, attachment to or chemisorption onto said metal; and in case where the electrode is made of glass, represent methoxy or alkoxy silane residues which are capable of chemical association, attachment to or chemisorption onto said glass;

$R^1$ represents a connecting group;

Q is a functional group which is capable of forming a covalent bond with a moiety in the catalytic peptide or in the porphyrin group.

Z, where the electrode material is a metal, may for example be a sulphur atom obtained from a thiol group, a disulfide group, a sulphonate group, or a sulphate group.

$R^1$ may be a covalent bond or may be a peptide or polypeptide or may be selected from a very wide variety of suitable groups such as alkylene, alkenylene, alkynylene phenyl containing chains, and many others.

Particular examples of $R^1$ are a chemical bond or a group having the following formulae (IIa), (IIb), (IIc) or (IId)

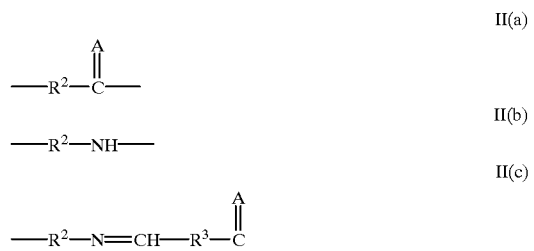

II(d)

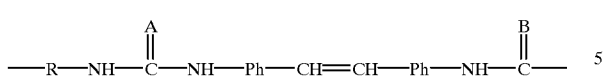

wherein $R^2$ or $R^3$ may be the same or different and represent straight or branch alkylene, alkenylene, alkynylene having 1-16 carbon atoms or represent a covalent bond, A and B may be the same or different and represent O or S, Ph is a phenyl group which is optionally substituted, e.g. by one or more members selected from the group consisting of $SO^{3-}$ or alkyl groups.

Q may for example be an amine group, capable of binding to a carboxyl residue; a carboxyl group, capable of binding to an amine residue; an isocyanate or isothiocyanate group or an acyl group capable of binding to an amine residue; or a halide group capable of binding to hydroxy residues of the polypeptide. Particular examples are the groups —$NH_2$— COOH; —N=C=S; N=C=O; or an acyl group having the formula —$R^a$—CO—G wherein G is hydrogen, a halogen such as Cl, or is OH, $OR^b$, a

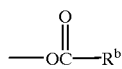

group or a

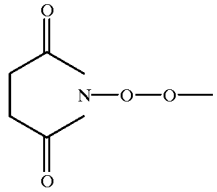

group; $R^a$ and $R^b$ being, independently a $C_1$–$C_{12}$ alkyl or alkenyl or a phenyl containing chain which is optionally substituted, e.g. by halogen.

Particular examples of such a linking group are those of the following formulae (III)–(IX):

| Z | $R^1$ | Q | |
|---|---|---|---|
| | | | (III) |

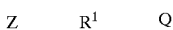

(IV)

(V)

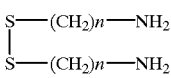

(VI)

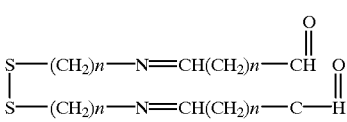

(VII)

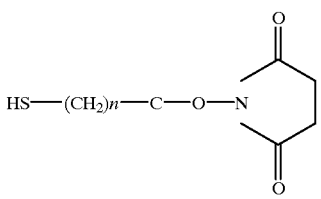

(VIII)

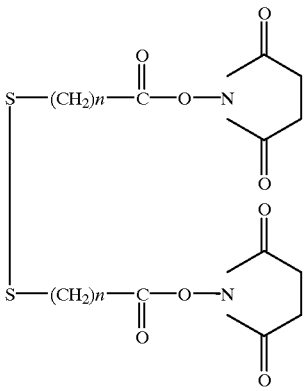

(IX)

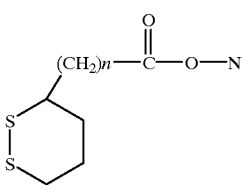

wherein n is an integer between 1–6.

Linking the FAD with an electro mediator group or a photoisomerizable group, as well as linking of electron mediators directly onto the enzyme, may be achieved by means of a connecting group having the following formula (X):

$$Z-F-R^1-Q \quad (X)$$

wherein $R^1$ has the same meaning as indicated above and $Q^1$ and $Q^2$ have independently one of the meanings given above for Q.

Examples of electron-mediator groups which can be used in accordance with the invention are errocene, pyrroloquinoline quinone, quinone, N,N'-dialkyl-4,4'-bipyridinium salts and many others.

The linking group may at times comprise also another functional group, such as an electron mediator group or a photoisomerizable group. A linking group in accordance with such embodiments may have the following general formula (XI)

$$Q^1-R^1-Q^2 \quad (XI)$$

wherein Z, $R^1$ and Q have the meaning given above, and F is the functional group.

Examples of photoisomerizable groups that can be used in accordance with the invention are nitrospiropyran, azobenzene, thiophene fulgide and many other compounds being photoisomerized from one state to the other state and back by irradiation by light of two different wavelength regions.

The present invention will now be further illustrated in the following specific embodiments and drawings.

BRIEF DESCRIPTION OF THE DRAWINGS

FIG. 7 shows the scheme of modification of a gold electrode with an FAD monolayer and the bioelectrocatalytic glucose oxidation using these enzyme electrodes;

(i) FAD-SP-GOD (●); (ii) FAD-MRH+-GOD (○).

Figure 17:
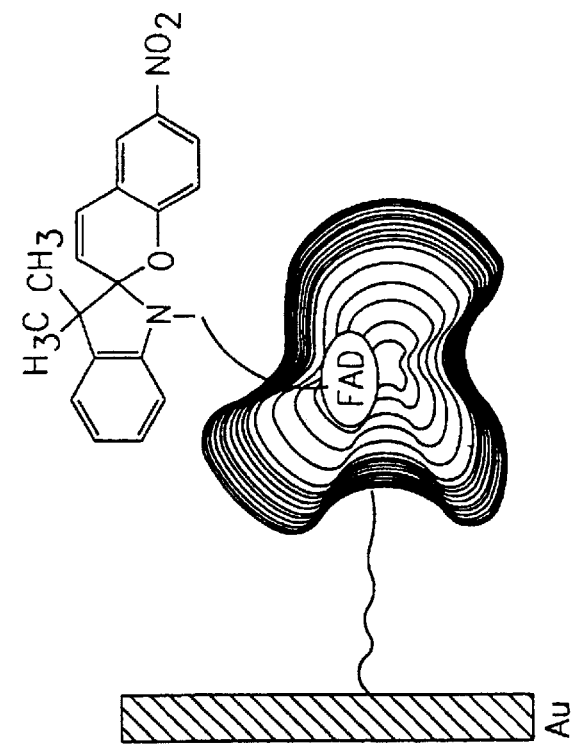
Figure 17:
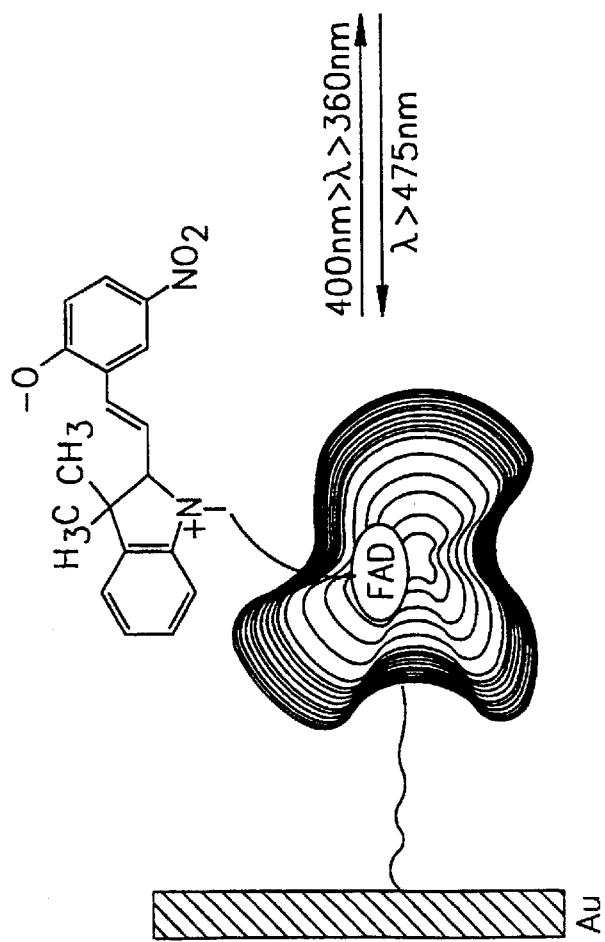

FIG. 17 shows the different isomeric forms providing "ON" (left) and "OFF" (right) states for the monolayer immobilized FAD-SP-GOD.

Figure 18:
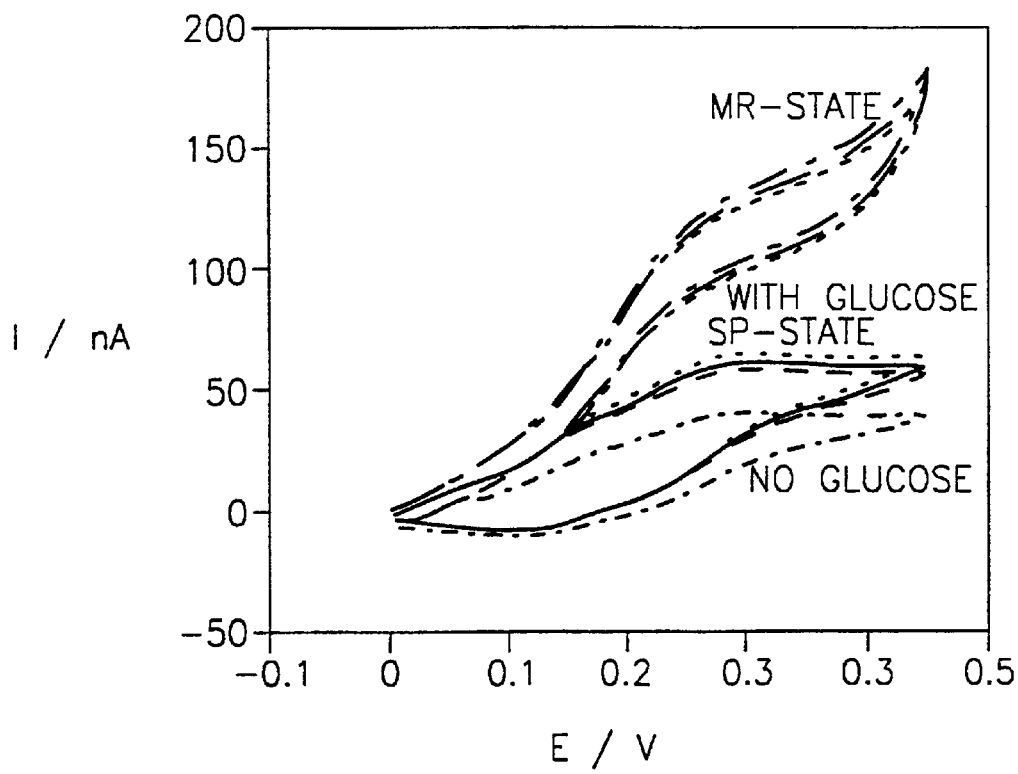

FIG. 18 shows cyclic voltammograms of different electroenzymatic activities for glucose oxidation by monolayer immobilized FAD-SP-GOD being in different isomeric states. Glucose concentration, 50 mM. Potential scan rate, 5 mV $s^{-1}$.

Figure 19:
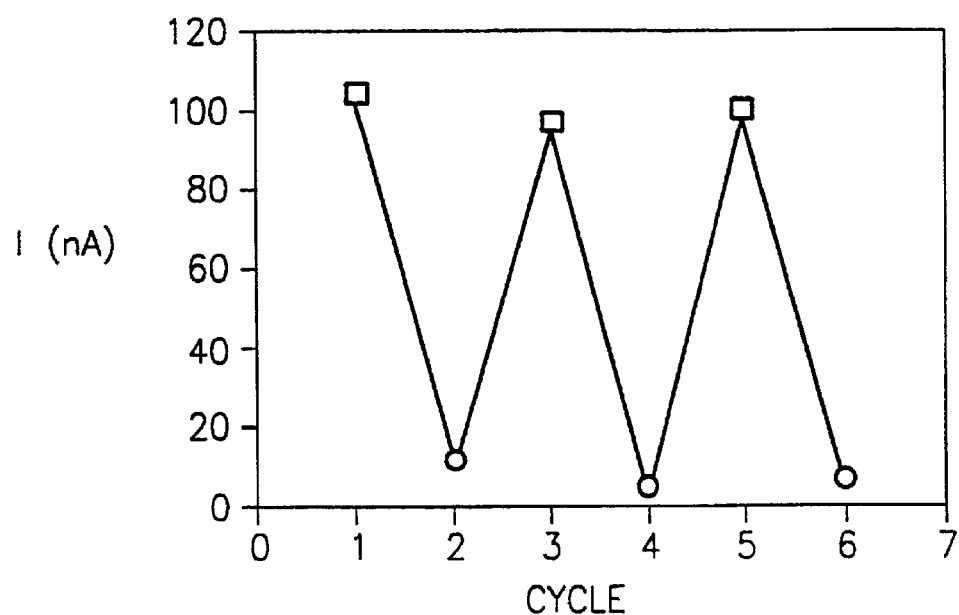

FIG. 19 shows cyclic amperometric transduction of optical signals recorded by the reconstituted photoisomerizable GOD monolayer immobilized onto a gold electrode; (○) SP-state, (□) MRH$^+$-state.

Figure 20:
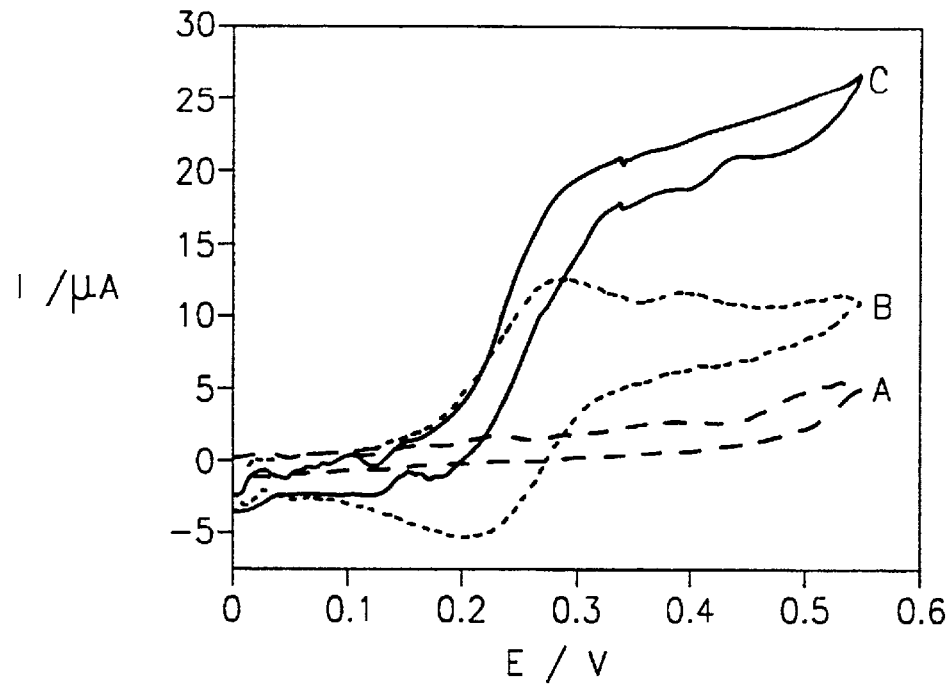

FIG. 20 shows cyclic voltammograms of GOD reconstituted onto a FAD-modified monolayer Au electrode: (a) background electrolyte solution only; (b) in the presence of ferrocene carboxylic acid, $4 \cdot 10^{-4}$ M; (c) with ferrocene carboxylic acid and added glucose, $5 \cdot 10^{-2}$M. All experiments were recorded under argon in 0.01 M phosphate buffer and 0.1 sodium sulfate, pH 7.0, 35° C., scan rate 5 mV $s^{-1}$.

Figure 21:
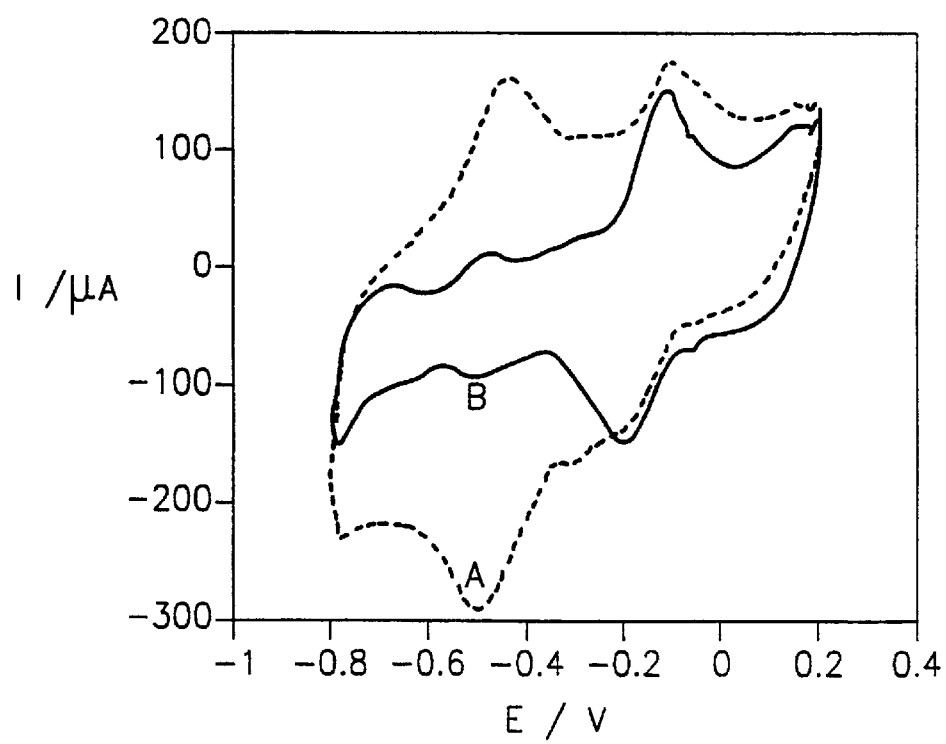

FIG. 21 shows cyclic voltammograms of the PQQ-FAD diad monolayer Au electrode (a) and of the PQQ-FAD diad monolayer after reconstitution with apo-GOD (b). All experiments were recorded under argon in 0.01 M phosphate buffer and 0.1 sodium sulfate, pH 7.0, 25° C., scan rate 50 mV $s^{-1}$.

Figure 22:
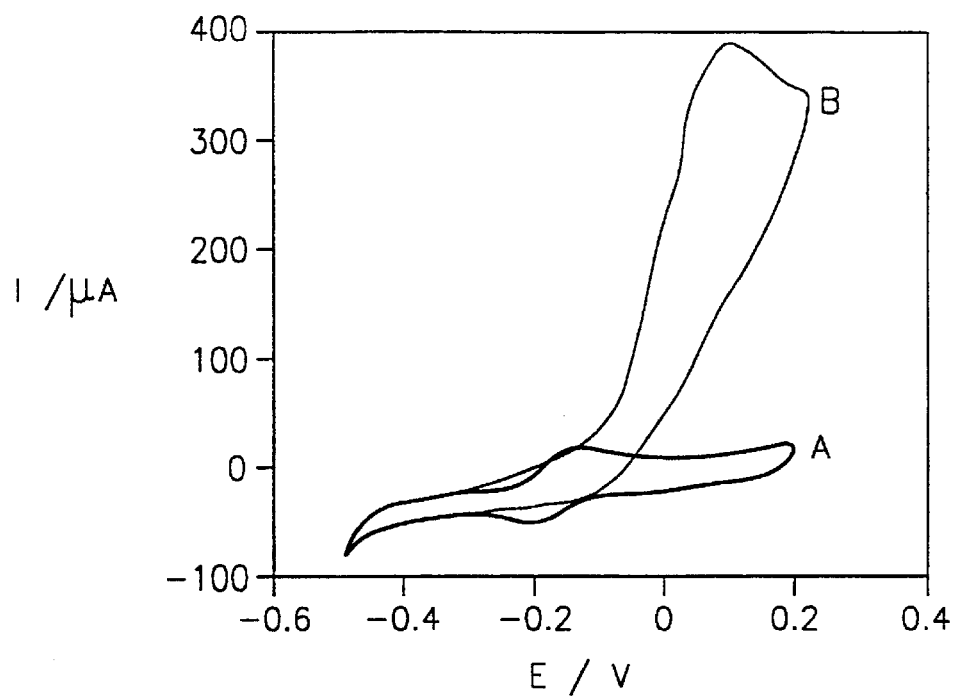

FIG. 22 shows cyclic voltammograms of GOD reconstituted onto the PQQ-FAD diad monolayer electrode; without glucose (a) and in the presence of 80 mM glucose (b). All experiments recorded under argon in 0.01 M phosphate buffer and 0.1 sodium sulfate, pH 7.0, 35° C., scan rate, 5 mV $s^{-1}$.

Figure 23:
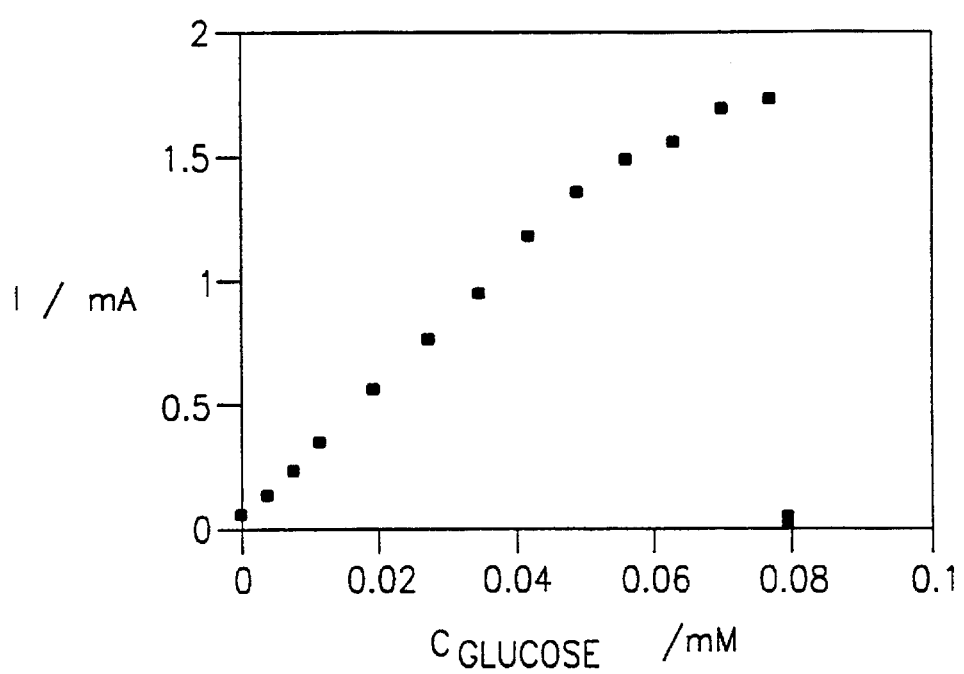

FIG. 23 shows amperometric responses of GOD reconstituted onto the PQQ-FAD diad monolayer electrode at different glucose concentration. Currents determined by chronoamperometry at final potential +0.2 V, 35° C..

Figure 24:
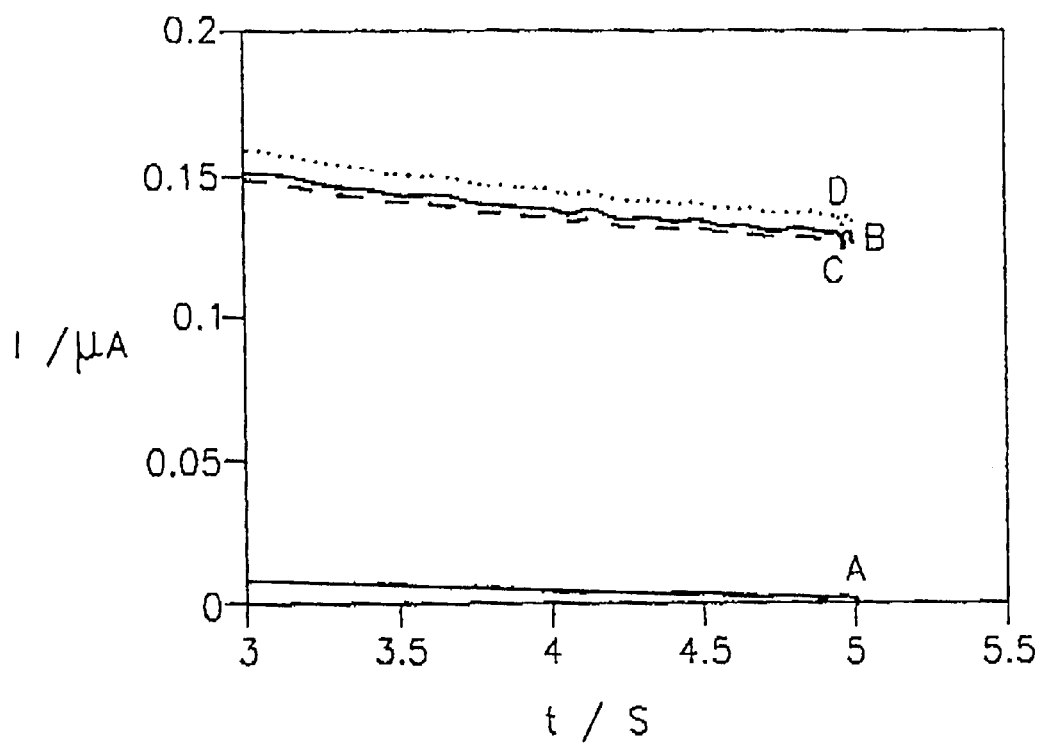

FIG. 24 shows an amperometric response produced by GOD reconstituted onto a PQQ-FAD monolayer: (a) in the absence of glucose; and (b) in the presence of 50 mM glucose, in the absence of $O_2$; (c) in the presence of 50 mM glucose in a solution saturated with air; (d) in the presence of 50 mM glucose, 0.1 mM ascorbic acid in a solution saturated with air. Currents were determined by chronoamperometry at a final potential of 0.0V vs. SCE. The electrolyte consisted of 0.01 M phosphate buffer and 0.1 M sodium sulfate, pH 7.0, with the measuring temperature being 35±0.5° C.

DESCRIPTION OF SPECIFIC EMBODIMENTS

The following specific embodiments are intended to illustrate the invention and shall be construed as limiting its scope. The artisan will no doubt appreciate that these specific embodiments are an example of the full scope of the invention as defined above.

EXAMPLES

Figure 1:
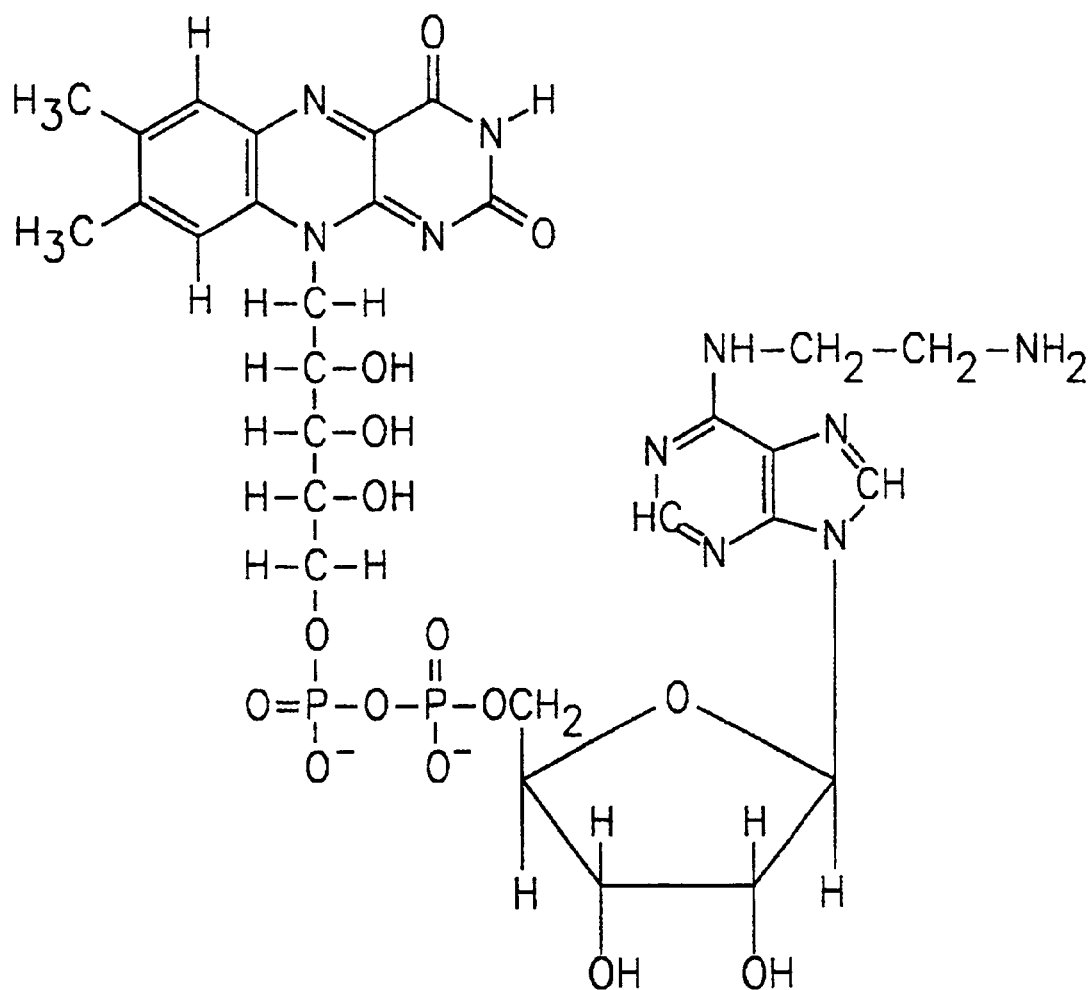
FIG. 1 shows the structure of $N^6$-(2-aminoethyl)-FAD.
Figure 2A:
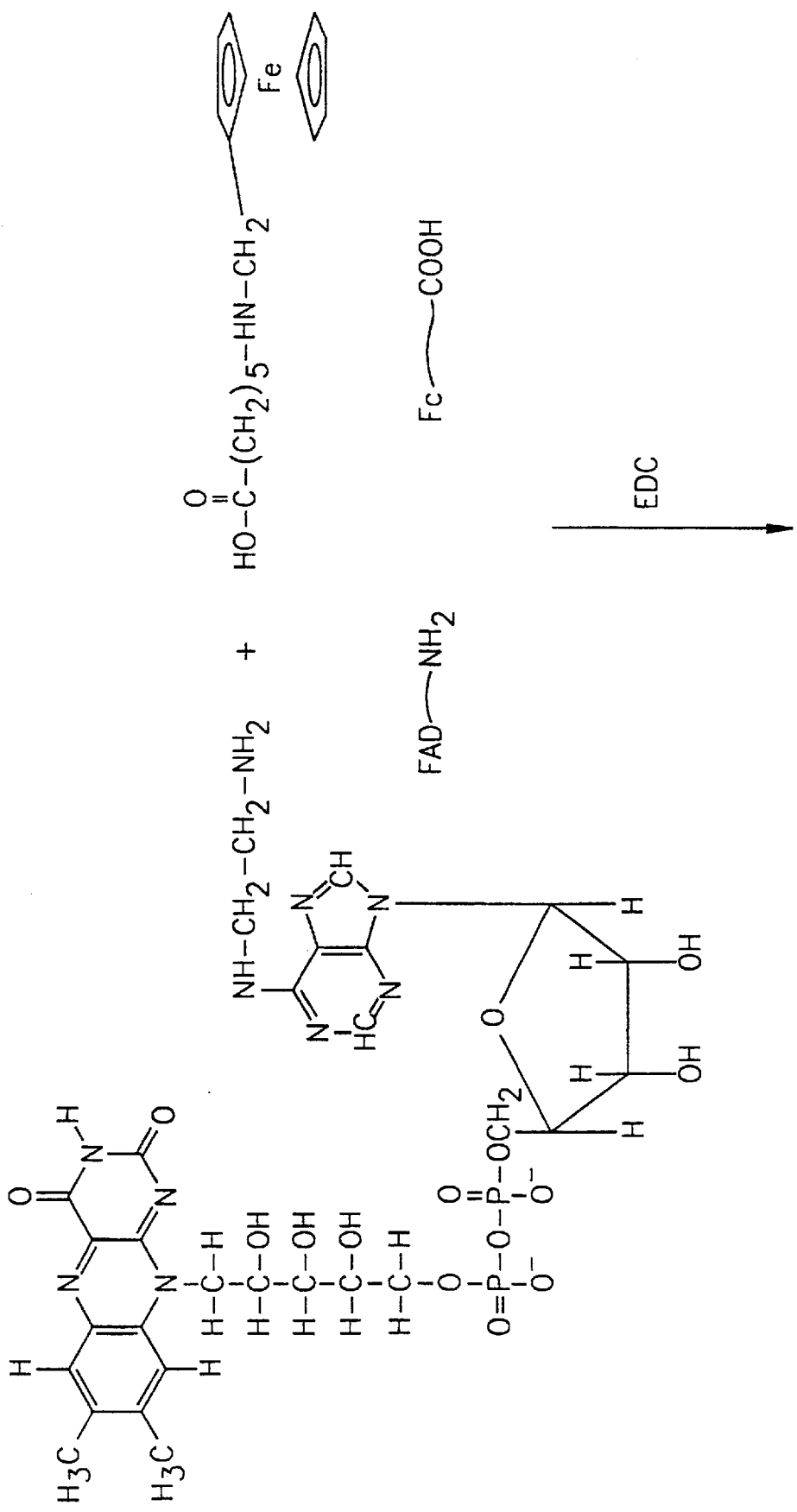
FIGS. 2A and 2B show the last synthetic step in preparation of FAD-ferrocene diad.
Figure 2B:
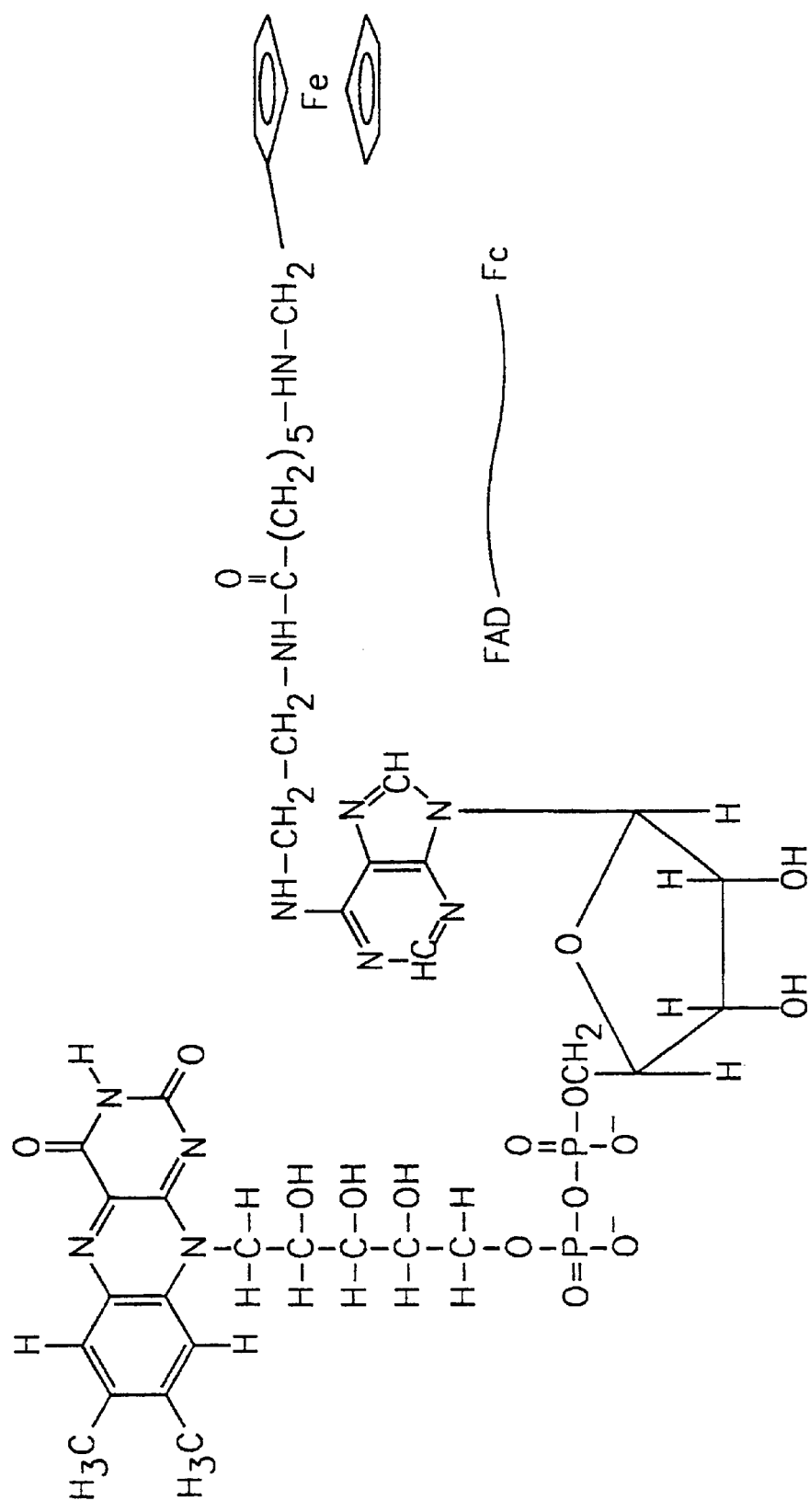

1. Chemical Synthetic Steps and Biochemical Preparations
   1.1 Last Synthetic Step in Preparation of FAD-Ferrocene Derivative Amino derivatized FAD, $N^6$-(20aminoethyl)-FAD, (FIG. 1) was synthesized according to the results published recently procedure[10]. N-(2-methylferrocene) caproic acid was synthesized as recently described[7]. $N^6$-(2-aminoethyl)-FAD (10 mg, $1.1 \cdot 10^{-5}$ mol) was reacted with N-(2-methyl-ferrocene) caproic acid (18 mg, $5.5 \cdot 10^{-5}$ mol) in the presence of 1-ethyl-3-(3-dimethylaminopropyl) carbodiimide (EDC, Aldrich; 11.6 mg, $5.5 \cdot 10^{-5}$ mol) as a coupling reagent and N-hydroxy-3-sulfosuccinimide sodium salt (NSI, Aldrich; 13.2 mg, $5.5 \cdot 10^{-5}$ mol) as a promoter (FIG. 2). The coupling reaction was done in 1 ml of 0.1 M HEPES buffer, pH 7.4 for 3 h at room temperature. The product was purified on Sepadex G10 column using water as eluent. The separation from the non-reacted original compounds was performed by a thin layer chromatography (TLC) $R_g$=0.49, 0.69, 0.93 for amino-FAD, Fc-COOH and the diad FAD-Fc, respectively). The structure of FAD-Fc was confirmed by $H^1$-NMR spectrum.

1.2 Last Synthetic Step in Preparation of FAD-Spiropyran derivative

Figure 3A:
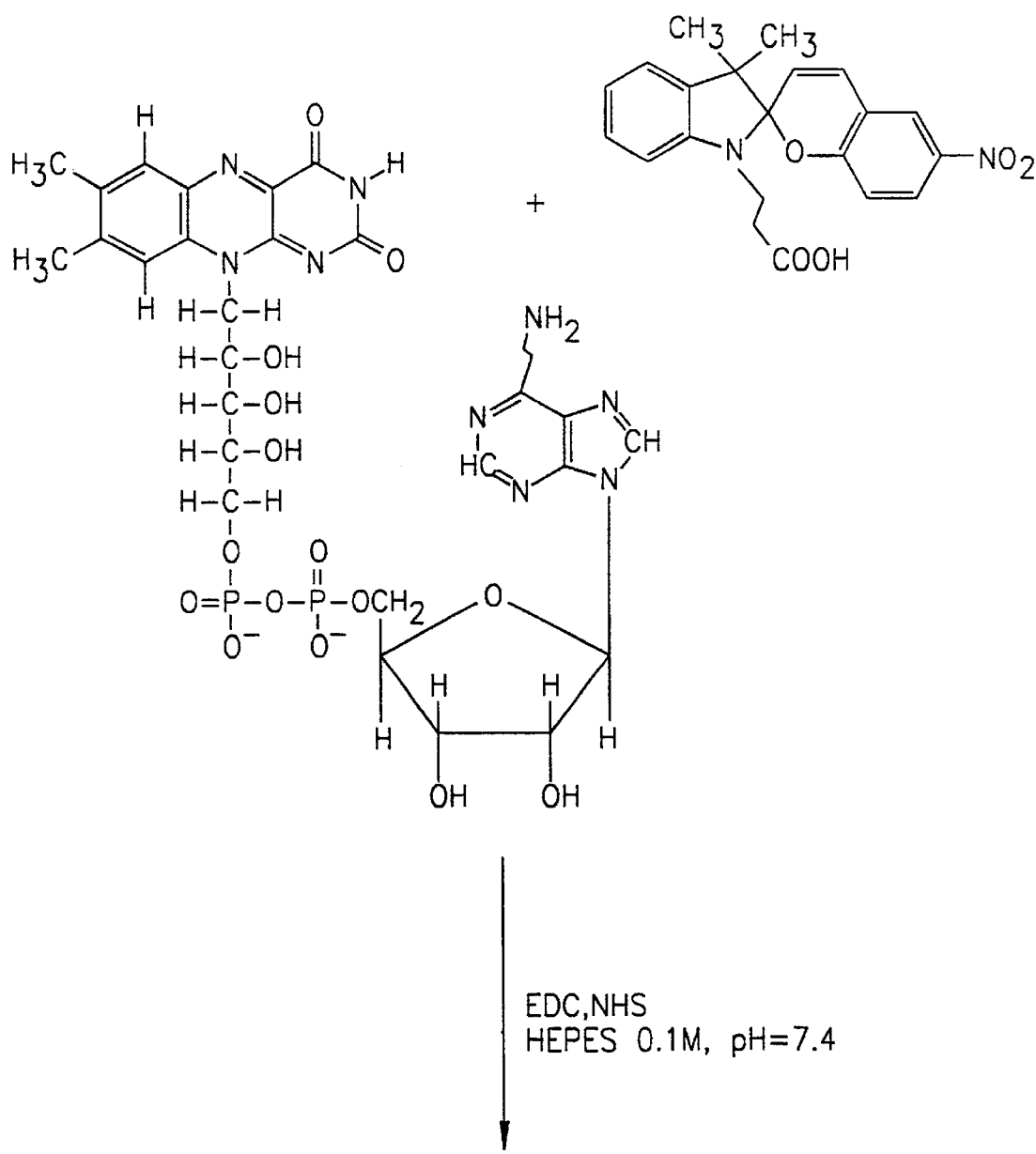
FIG. 3A shows the last synthetic step in preparation of FAD-spiropyran diad (FAD-SP).
Figure 3B:
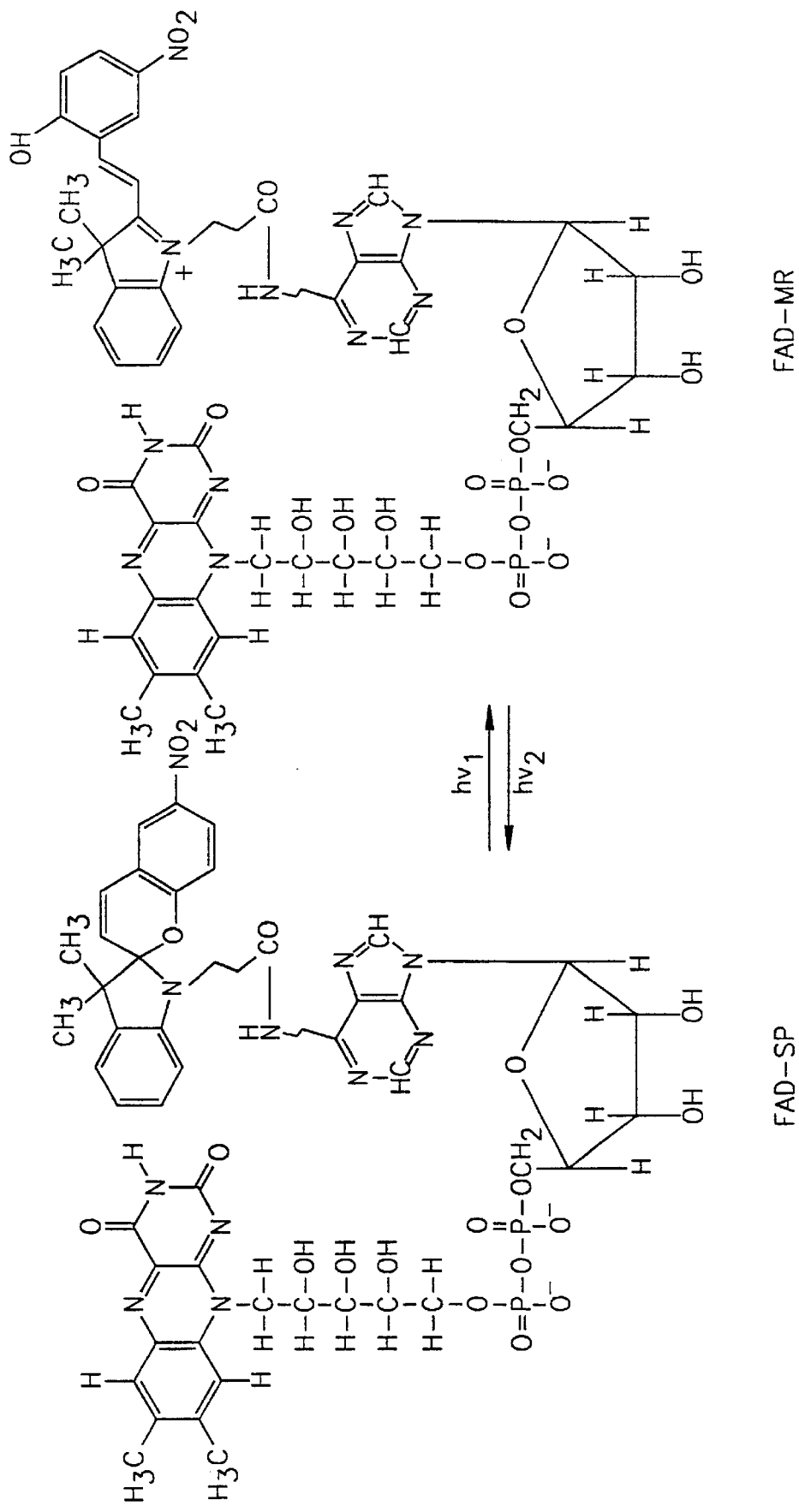
FIG. 3B shows the two photoisomeric states of the FAD-SP.

Carboxylic derivative of spiropyran, 1'-(β-carboxymethyl)-3',3'-dimethyl-6-nitro-[2H-1]benzopyran-2,2'-indolin, SP-COOH, was synthesized as hitherto described (Namba and Suzuki, *Bul. Chem. Soc. Jpn*, 48:1323, 1975)[13]. The diad including the amino-FAD and the photoisomerizable component (FAD-SP) was prepared similarly as described above for FAD-Fc using SP-COOH as carboxylic component for coupling with the amino-FAD (FIG. 3). The product was purified by preparative TLC on $SiO_2$ plates using isopropanol:$H_2O$ (7:3) as eluent. The nitrospiropyran-modified FAD reveals reversible photoisomerizable properties. Illumination of FAD-SP, 360 nm<λ<380 nm ("hv" in FIG. 3), yields the nitromerocyanine-FAD isomer state, FAD-MRH$^+$, exhibiting an absorption band in the region of 320–560 nm that corresponds to the overlapping bands of the MRHP$^+$ (520 nm) and FAD (355 nm, 460 nm) chromophores. Irradiation of the MRH$^+$-FAD solution, λ>475 nm ("hv$_1$" in FIG. 3) yields a yellow solution exhibiting the FAD absorption band at λ=360 nm, 447 nm and the characteristic SP-absorption in the UV region. The photoisomerization between the FAD-SP and FAD-MRH$^+$ is reversible (FIG. 3).

1.3 Apo-Enzyme Preparations

Apo-glucose oxidase (apo-GOD) was prepared similarly as hitherto described (Morris and Buckler in *Methods in Enzymology*, Vol. 92, Part E, (J. J. Langone and V. Van Vunakis, Eds.), Academic Press, Inc. pp. 415–417, 1983) by acidification of a glucose oxidase, GOD, solution (from *Aspergillus nigger*, E.C. 1.1.3.4) to pH=1.7, followed by separation on a Sephadex G-25 column and further purification with charcoal-dextran, and dialysis against 0.1 M phosphate buffer, pH 7.0, for 24 hours at 4° C..

Apo-protein derived from D-aminoacid oxidase (DAAO; from pig kidney, E.C. 1.4.3.3) was prepared following a similar procedure as hitherto described (Massey and Curti, *J. Biol. Chem.*, 241:3417, 1966) as follows: The enzyme was dialyzed against a 0.1 M pyrophosphate buffer, pH 8,5, containing 1 M KBr and $3 \cdot 10^{-3}$ MEDTA, followed by dialysis against a 0.1 M pyrophosphate buffer, pH 8,5, and finally it was purified by the same way as apo-GOD. Both apo-proteins do not show any enzymatic activity.

1.4 Reconstitution of Apo-Enzymes with Diads: FAD-FC and FAD-SP

Figure 4:
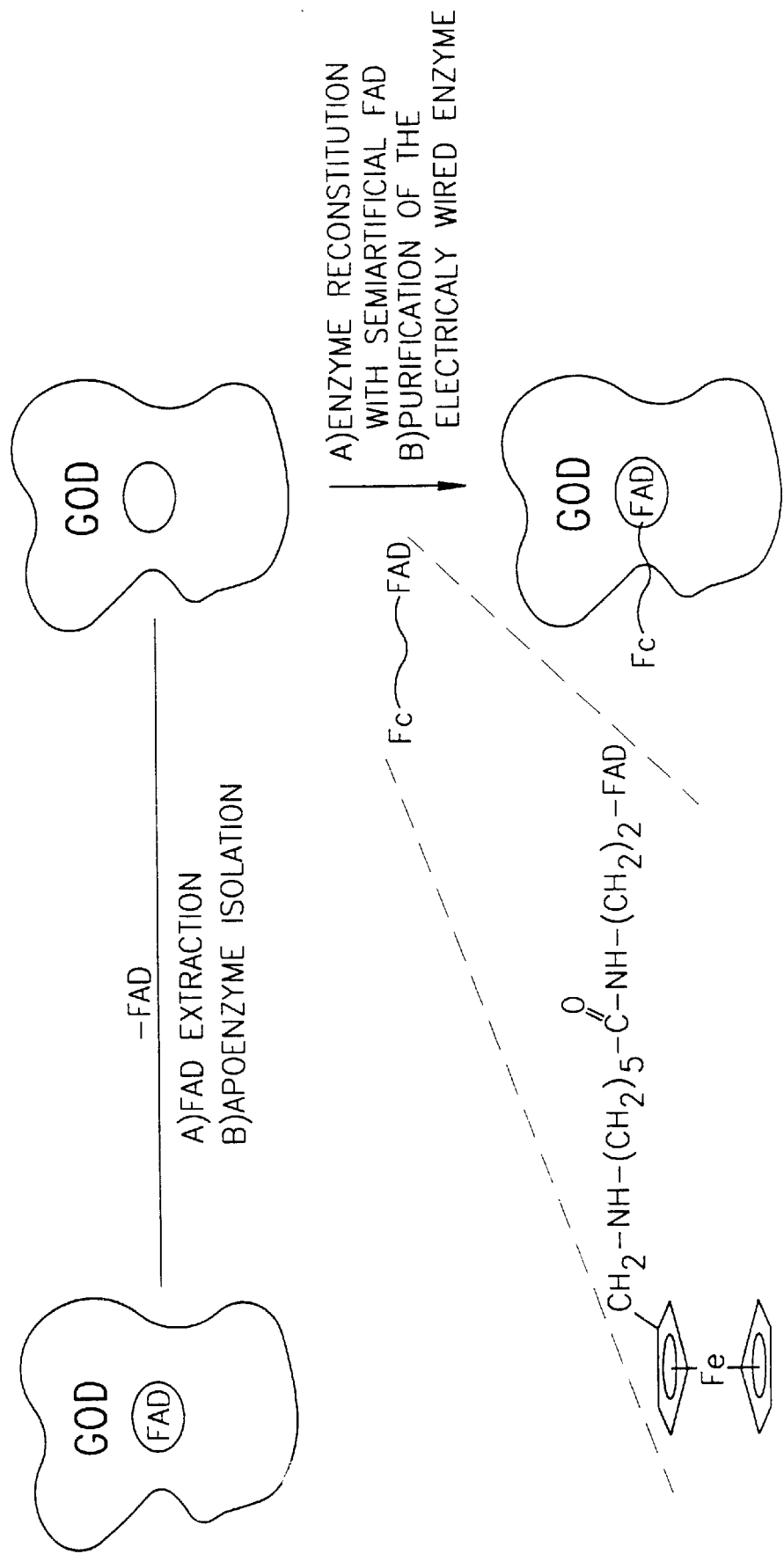
FIG. 4 shows the preparation of glucose oxidase apoenzyme and its reconstitution with FAD-ferrocene diad.

The apo-GOD was reacted with FAD-Fc diad to generate the ferrocene-FAD reconstituted glucose oxidase (FIG. 4). The reconstitution was done in 3 ml stirred Na-phosphate buffer, 0.1 M, pH 7:0, containing 9.6 mg ($5.16 \cdot 10^{-5}$ mol) apo-GOD and 0.8 mg ($6.7 \cdot 10^{-4}$ mol) FAD-Fc for 4 h at room temperature followed by overnight incubation at 4° C.. The solution was purified twice by filtration through a filter with a cut of 10,000 and then dialyzed against 0.1 M Na-phosphate buffer, pH 7.0 for one day.

The loading of the reconstituted GOD was determined spectroscopically as one molecule of the FAD-Fc diad per the enzyme subunit. The activity of the reconstituted GOD was about 40% of that of the native GOD.

The apo-DAAO was reconstituted with the FAD-Fc diad and then purified similarily as described above for the apo-GOD. The loading of the reconstituted DAAO was about one molecule of the FAD-Fc diad per the enzyme. The activity of the reconstituted GOD was about 20% of that of the native GOD.

Figure 5A:
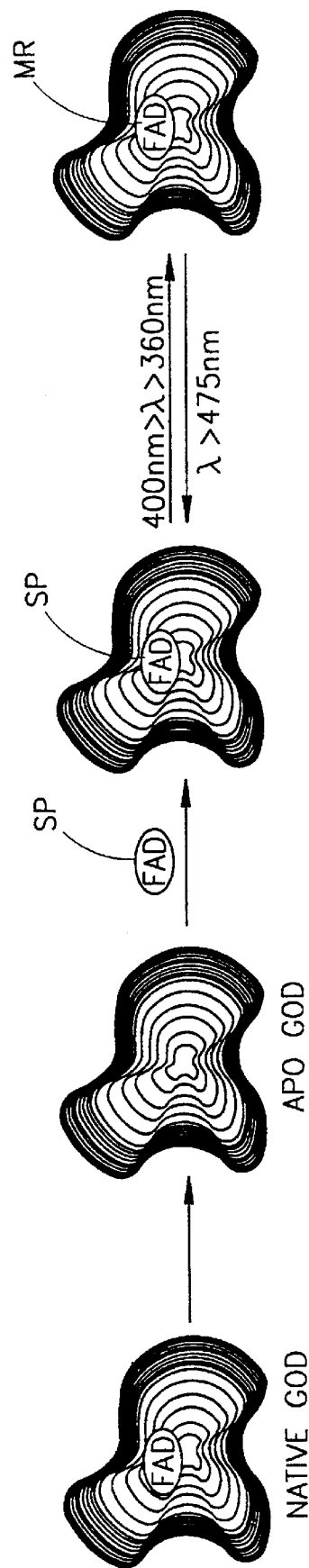
FIG. 5A shows the preparation of glucose oxidase apoenzyme and its reconstitution with FAD-spiropyran diad and the photoisomerization of the reconstituted enzyme.
Figure 5B:
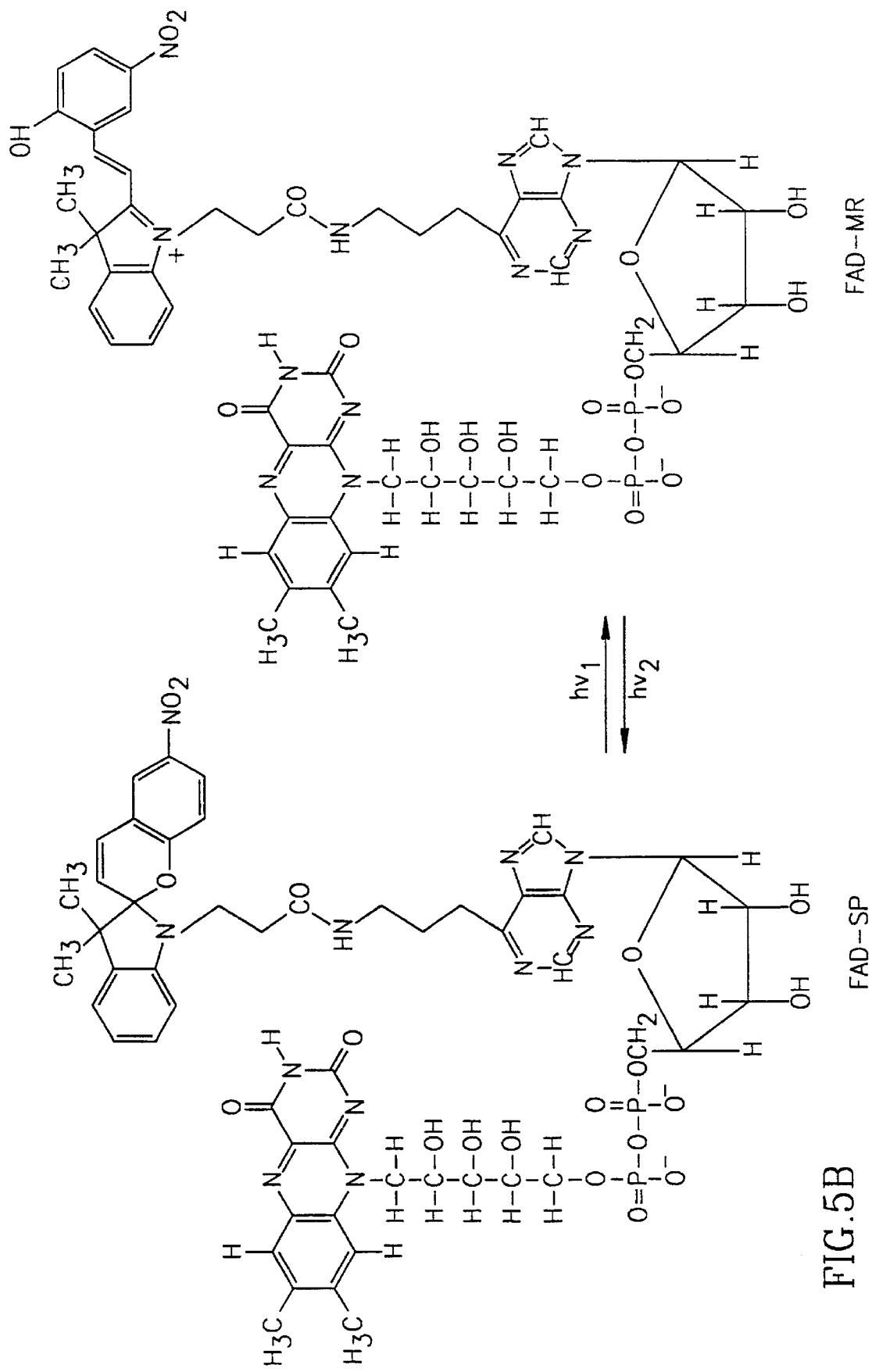
FIG. 5B shows the two photoisomeric states of the modified FAD.

Reconstitution of the apo-GOD with the FAD-SP diad (FIG. 5) was accomplished by treatment of apo-GOD with the diad (molar ratio 1:10) in 0.1 M phosphate buffer, pH 7.0 under vigorous shaking for 24 hours, 25° C.. The product was dialyzed against phosphate buffer, 0.1 M, pH 7.0, for 30 hours. The loading of the FAD-SP cofactor was about 1 per each of the enzyme subunits. Reconstituted GOD exhibits about 80% of the activity of the native GOD. The reconstituted GOD exhibits photoisomerizable properties. Illumination of the GOD reconstituted with FAD-SP, 360 nm <λ<380 nm, yields the merocyanine isomeric state that can be isomerized back using illumination λ>475 nm (FIG. 5).

2. Electrode Characterization and Electrochemical Set-Ups

Gold electrodes (0.5 mm diameter Au wire, having a geometrical area of about 0.2 cm$^2$; roughness coefficient of about 1.2 or Au foil of geometrical area of about 0.4 cm$^2$; roughness coefficient of about 15) were used for all modifications and measurements. The rough gold electrode was obtained by treatment with liquid mercury and further dissolution of the amalgam layer in concentrated nitric acid (Katz et al., *J. Electroanal. Chem.*, 367:59, 1994). A cyclic voltammogram recorded in 0.5 M $H_2SO_4$ was used to determine the purity of the electrode surface just before modification. The real electrode surface area and coefficients of roughness were estimated from the same cyclic voltammogram by integrating the cathodic peak for the electrochemical reduction of the oxide layer on the electrode surface (Woods in A. J. Bard (Ed.), Electroanalytical Chemistry, Dekker, New York, p. 1, 1978).

Electrochemical measurements were performed using a potentiostat (EG&G) VersaStat) connected to a personal computer (EG&G research electrochemistry software model 270/250). All the measurements were carried out in a three-compartment electrochemical cell comprising the chemically modified electrode as a working electrode, a glassy carbon auxiliary electrode isolated by a glass frit and a saturated calomel electrode (SCE) connected to the working volume with a Luggin capillary. All potential are reported with respect to this reference electrode. Argon bubbling was used to remove oxygen from the solutions in the electrochemical cell. During the measurements the cell was thermostated using circulated water in a jacket around the cell (the temperature is indicated in each of the experimental examples below).

3. Electrode Modification 3.1 Pretreatment

To remove a previous organic layer and to regenerate a bare metal surface, the electrode was treated with a boiling 2 M solution of KOH for 1 h, then rinsed with water and stored in concentrates sulfuric acid. Immediately before modification, the electrode was rinsed with water, soaked for 10 min in concentrated nitric acid and then rinsed again with water.

3.2 Electrode Modification with Cystamine

A clean bare gold electrode was soaked in a solution of 0.02 M cystamine (2,2'-diaminodiethyldisulfide, Aldrich) in water for 2 h. The electrode was then rinsed thoroughly with water to remove the unabsorbed cystamine.

Figure 6:
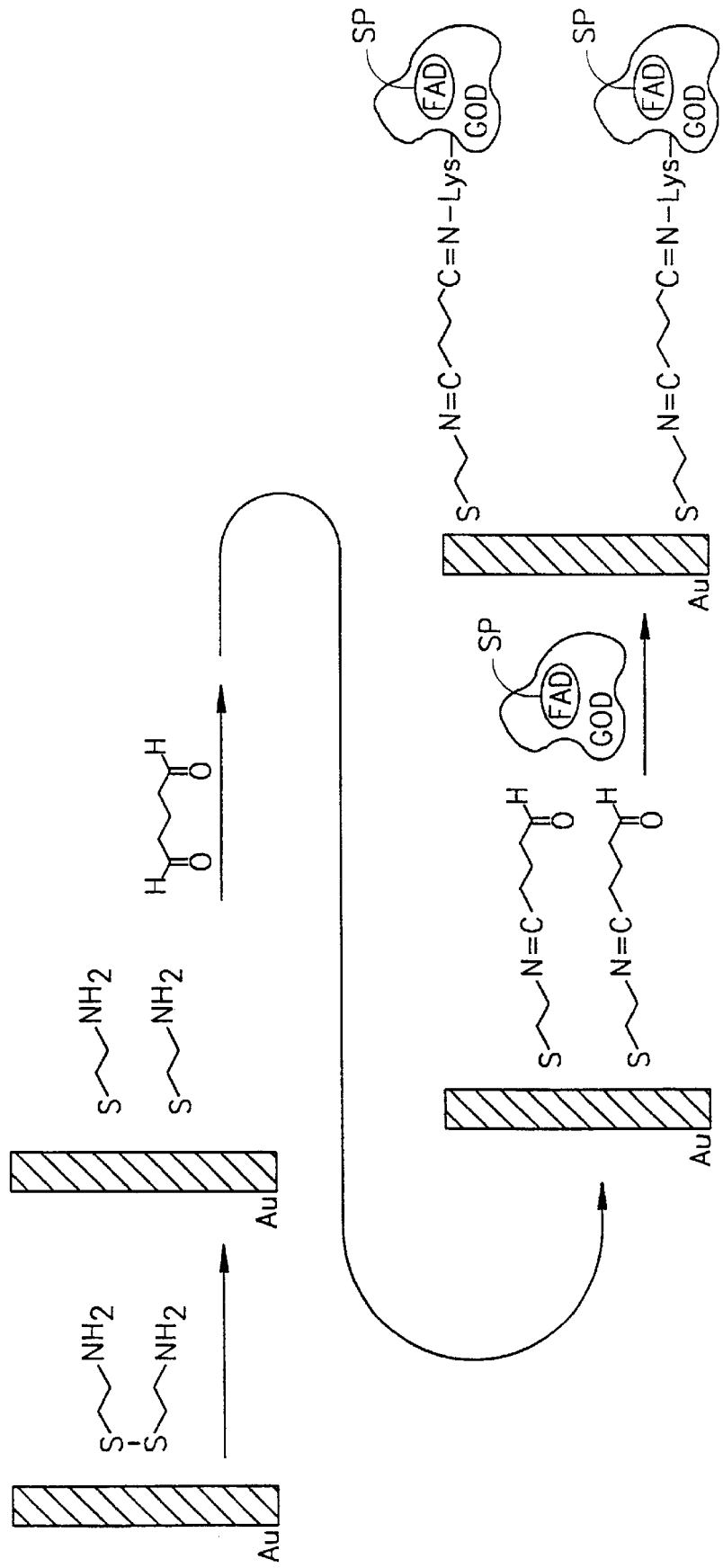
FIG. 6 shows the scheme of immobilization of GOD reconstituted with FAD-spiropyran diad, onto a gold electrode to form a GOD monolayer.

3.3 Monolayer Immobilization of the Photoswitchable GOD Reconstituted with FAD-SP A gold electrode was functionalized with active ester groups by chemisorption of dithio-bis-(succinimidylpropionate) (DSP, Aldrich) (Willner et al., 1992[2]; Katz, E., *J. Electroanal. Chem.*, 191:257, (1990)) and then the electrode was treated with the GOD reconstituted with FAD-SP (4 mg per 1 ml of 0.01 M phosphate buffer, pH 7.0) for 1 h (FIG. 6). The enzyme electrode was rinsed with 0.1 M phosphate buffer, pH 7.0 and used immediately for electrochemical measurements.

3.4 Electrode Modification with a FAD Monolayer

Figure 7A:
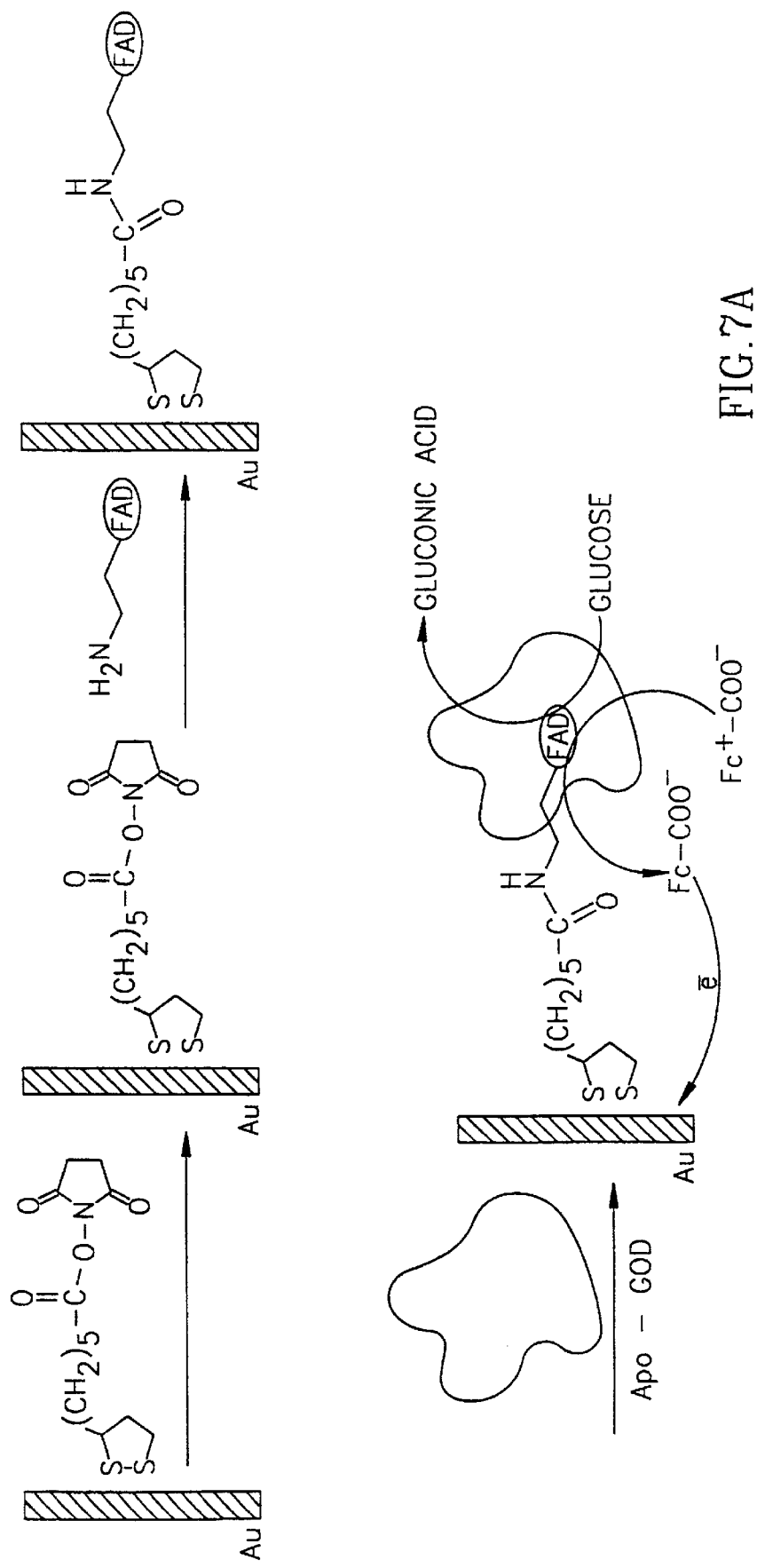
FIG. 7A shows an electrode in accordance with the first embodiment of the invention with electron mediator group freely tumbling in the medium.

A lipoic acid active ster monolayer was adsorbed (1 h, room temperature) onto a rough gold electrode from 10 mM solution in dimethylsulfoxide (DMSO). The resulting electrode was rinsed twice with DMSO and once with water to remove physically adsorbed molecules. Then the modified electrode was treated with 5 mM $N^6$-(2-aminoethyl)-FAD solution in 0.1 HEPES buffer, pH 7.3 for 1 h and finally rinsed several times with water (FIG. 7A).

3.5 Electrode Modification with a PQQ-FAD Monolayer

Figure 7B:
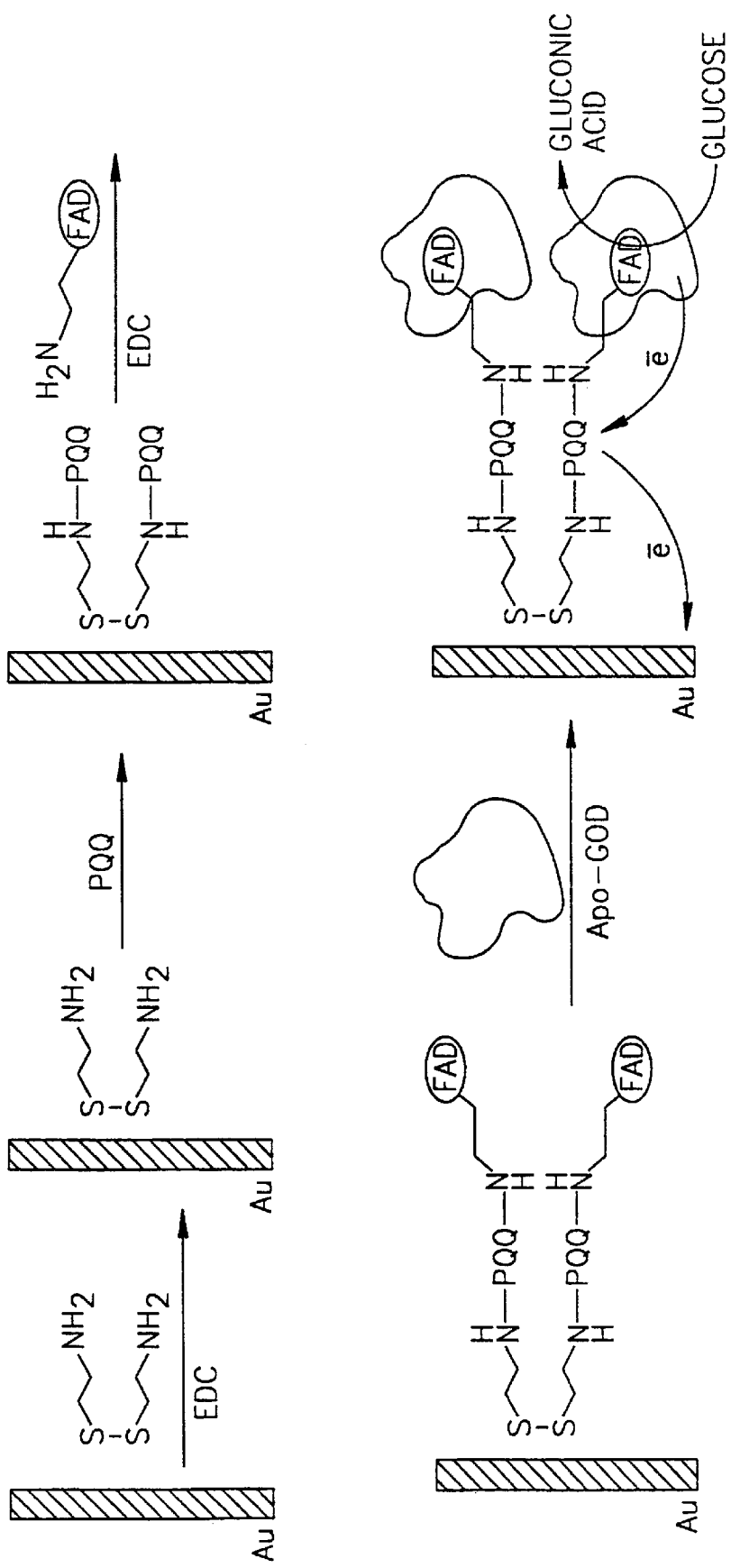
FIG. 7B shows an enzyme in accordance with the combined first and second embodiments with an electron mediator group (PQQ) covalently bound to the FAD group.
Figure 8:
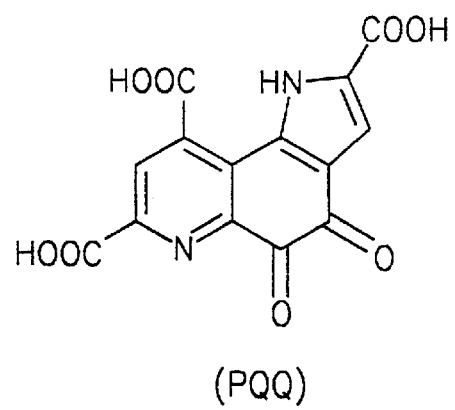
FIG. 8 shows the structure of pyrroloquinoline quinone (PQQ).

The electrode modification with pyrroloquinoline quinone, PQQ, (FIG. 8) was done as recently described[14]. A cystamine monolayer Au modified electrode was soaked for 3 h in a 0.01 M HEPES buffer solution, pH 7.3, containing 1 mM PQQ (Sigma). Then the modified electrode was thoroughly rinsed with water to remove from its surface uncoupled physically adsorbed PQQ molecules. The obtained PQQ-functionalized electrode was treated with 5 mM $N^6$-(2-aminoethyl)-FAD solution in 0.1 HEPES buffer, pH 7.3, in the presence of 10 mM EDC for 1 h and then thoroughly rinsed again with water (FIG. 7B).

3.6 Apo-GOD Reconstitution onto FAD or PQQ-FAD Functionalized Electrode Surfaces Each FAD-functionalized electrode (FAD only and PQQ-FAD) was treated with an apo-GOD solution (about 3 mg/ml in phosphate buffer, 0.1 M, pH 7.0) under vigorous shaking for 4 hours at room temperature and then for 16 hours at 4° C.. Then the modified electrode was rinsed with the 0.1 M phosphate buffer, pH 7.0 and used immediately for electrochemical measurements (FIGS. 7A&B).

4. Results 4.1 Electroenzyme: GOD Reconstituted with FAD-FC

Figure 9:
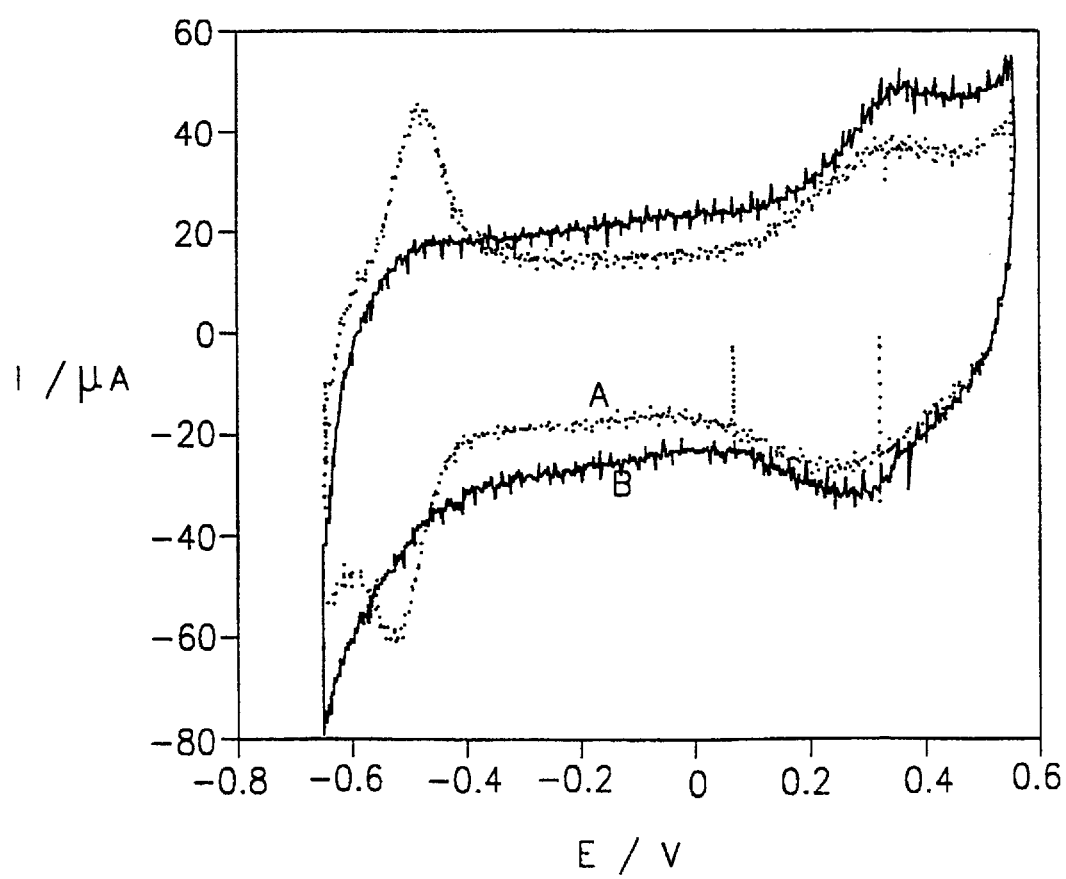
FIG. 9 shows cyclic voltammograms: (a) FAD-ferrocene (see FIG. 4) adsorbed onto an Au working electrode (from a $1 \cdot 10^{-5}$ M stock solution); (b) FAD-ferrocene reconstituted GOD in solution (1.75 mg $mL^{-1}$) (see FIG. 12) using a cystamine monolayer modified Au electrode. Background: 0.1 M phosphate buffer, pH 7.3, under argon. Potential scan rate, 1.5 V $s^{-1}$.

The FAD-Fc diad exhibits in an aqueous buffer solution two characteristic reversible waves at −0.50 and 0.35 V (vs SCE) (FIG. 9).

These waves correspond to the two-electron redox process of FAD and the one-electron redox reaction of the ferrocene, respectively. The electrochemical process shows strong adsorption of the FAD-Fc diad on the unmodified Au electrode. The cyclic voltammogram of the FAD-Fc-reconstituted GOD shows only the reversible redox process of the ferrocene unit, implying that the ferrocene component communicates with the electrode where the enzyme-embedded FAD component lacks direct electrical communication with the electrode (FIG. 9).

Figure 10:
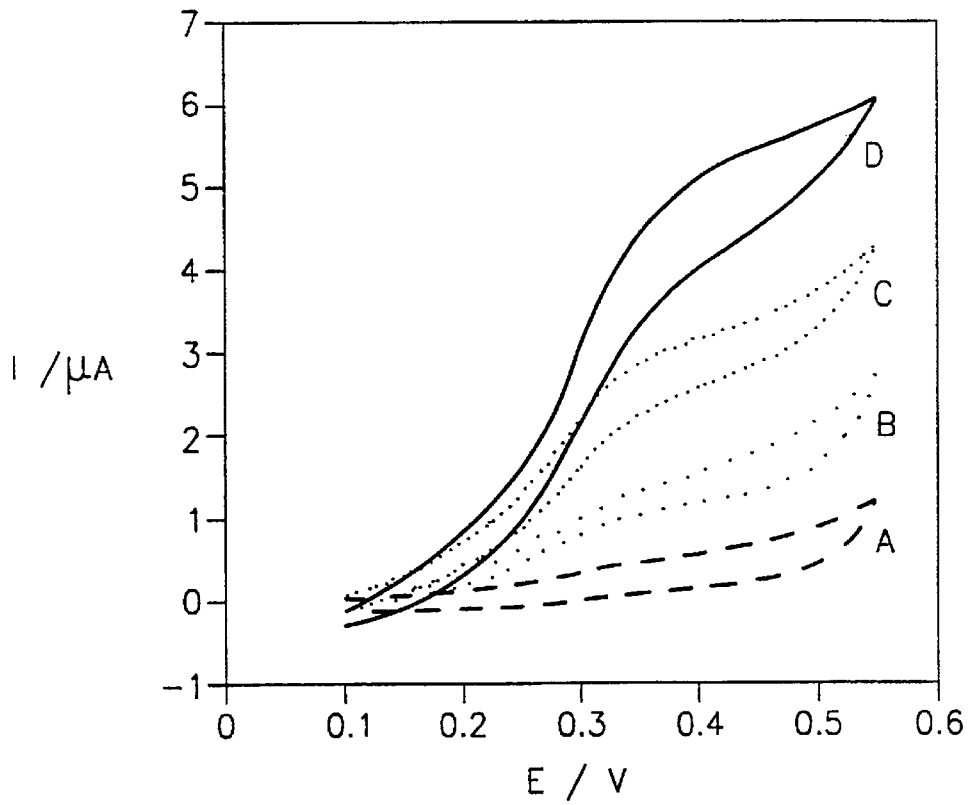
FIG. 10 shows cyclic voltammograms of FAD-ferrocene-reconstituted GOD in solution (1.75 mg $mL^{-1}$) and different concentrations of glucose: (a) 0 mM, (b) 1 mM, (c) 3 Mm, (d) 20.5 mM. All experiments were performed in 0.1 M phosphate buffer, pH 7.3, at 35° C.; under argon, using a cystamine modified Au electrode. Potential scan rate, 2 mV $s^{-1}$.
Figure 11:
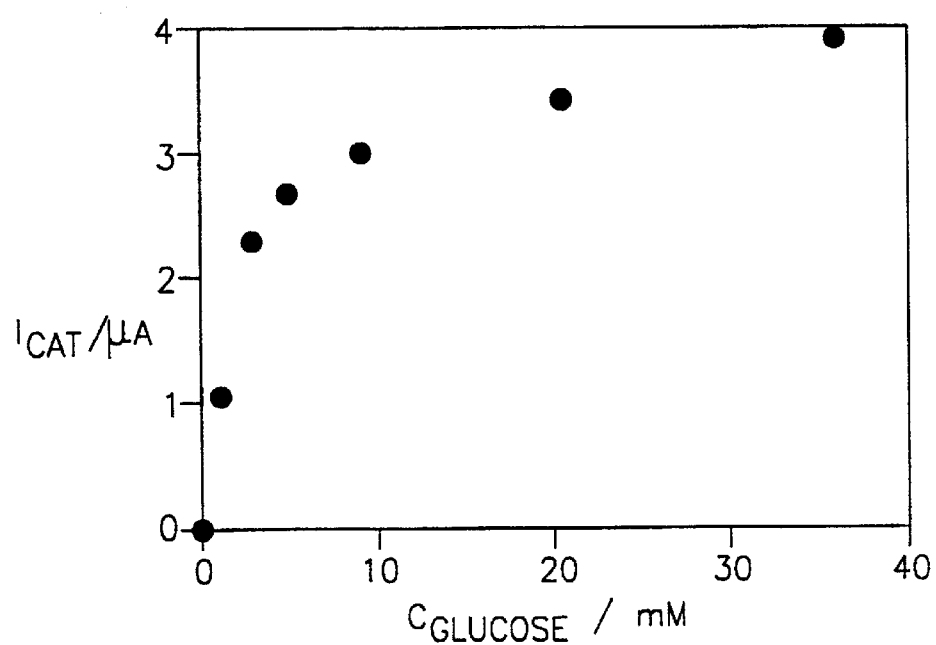
FIG. 11 shows the peak anodic currents at different glucose concentrations in an experiment such as that shown in FIG. 10.
Figure 12:
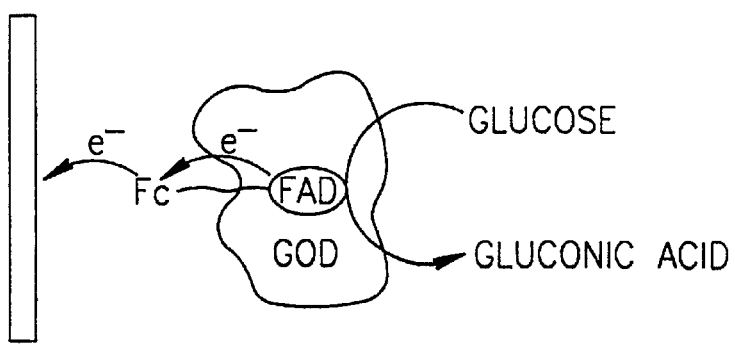
FIG. 12 shows the bioelectrocatalytic oxidation scheme of glucose using FAD-ferrocene reconstituted GOD ("electroenzyme").
Figure 13:
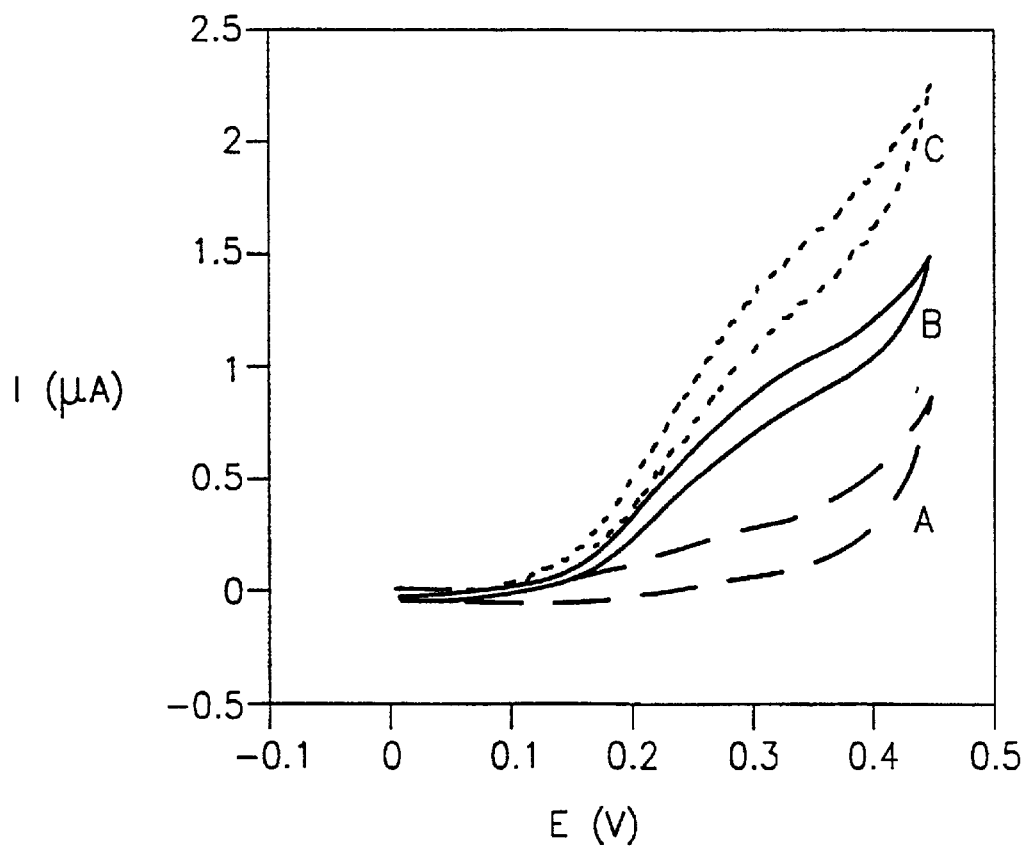
FIG. 13 shows cyclic voltammograms of FAD-ferrocene reconstituted D-aminoacid oxidase (DAAO) in solution (0.38 mg/ml) in the presence of D-alanine: (a) 0 mM, (b) 2 mM, (c) 9 mM. Experiment carried out in 0.1 M pyrophosphate buffer, pH 8.5; 25° C.; under argon. Potential scan rate, 2 mV $s^{-1}$.

A cystamine modified electrode was used for electrochemical measurements of the reconstituted GOD to prevent the protein adsorption that could result in the enzyme denaturation. FIG. 10 shows the electrocatalytic anodic currents developed by the FAD-Fc-reconstituted GOD in the presence of different concentrations of added glucose. The calibration curve, showing the anodic current at different concentrations, is given in FIG. 11. The electrobiocatalyzed oxidation of glucose can be analyzed in terms of the Michaelis-Menten model ($I_{max}$=4 $\mu$A and $K_m$=2.9 mM, where $I_{max}$ is the saturation current and $K_m$ is the Michaelis-Menten constant). Taking into account the surface area and roughness factor of the working electrode, this maximum current density corresponds to $I_{max}$=8.3 $\mu$A/cm$^2$. For comparison, native glucose oxidase under comparable conditions in the presence of ferrocene carboxylic acid yields the values $K_m$3.3 mM and $I_{max}$=6.3 $\mu$A/cm$^2$. It can thus be concluded that reconstitution of apo-GOD with the ferrocene-modified-FAD yields a semi-synthetic electroenzyme exhibiting electrical communication between the electrode and the biocatalyst active site (FIG. 12).

the reconstituted DAAO showed electrical communication with electrode surface and electrocatalytic anodic currents were observed in the presence of D-alanine as substrate. FIG. 13 shows the cyclic voltammograms observed upon addition of different concentrations of D-alanine to a solution that contains the FAD-Fc DAAO. The respective calibration curve was similarly analyzed in terms of the Michaelis-Menten model and the values $I_{max}$=3.96 $\mu$A/cm$^2$ and $K_m$=2.0 mM were derived for the semi-synthetic electroactive DAAO. Similar to the reconstituted GOD, this reconstituted enzyme thus also functions as an electroenzyme.

Figure 14:
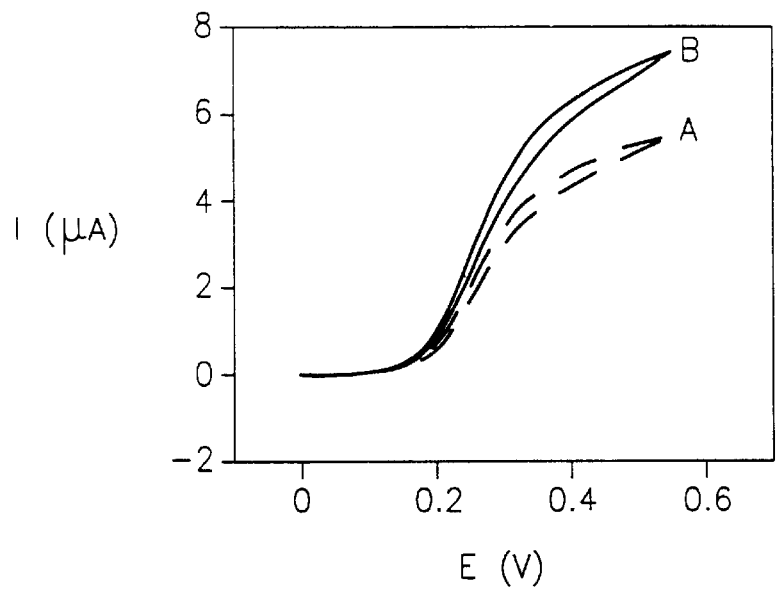
FIG. 14 shows cyclic voltammograms of the bioelectrocatalyzed oxidation of glucose, $5 \cdot 10^{-2}$ M, and ferrocene carboxylic acid, $5-10^{-4}$ M, in the presence of: (a) FAD-SP-GOD, 0.46 mg/ml, (b) FAD-MRH$^+$-GOD, 0.46 mg/ml. All experiments were recorded in a 0.1 M phosphate buffer, pH 7.0, 37° C., under argon. Potential scan rate, 5 mV $s^{-1}$.
Figure 15:
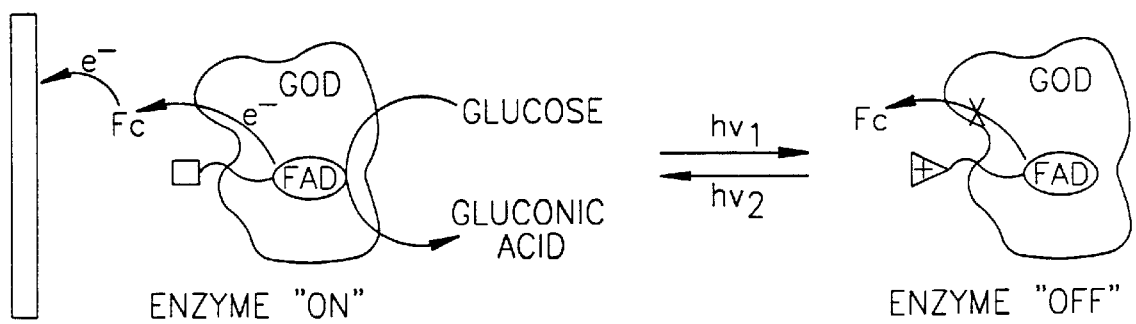
FIG. 15 shows bioelectrocatalytic oxidation schemes of glucose using FAD-SP reconstituted GOD (photoswitchable enzyme).
Figure 16:
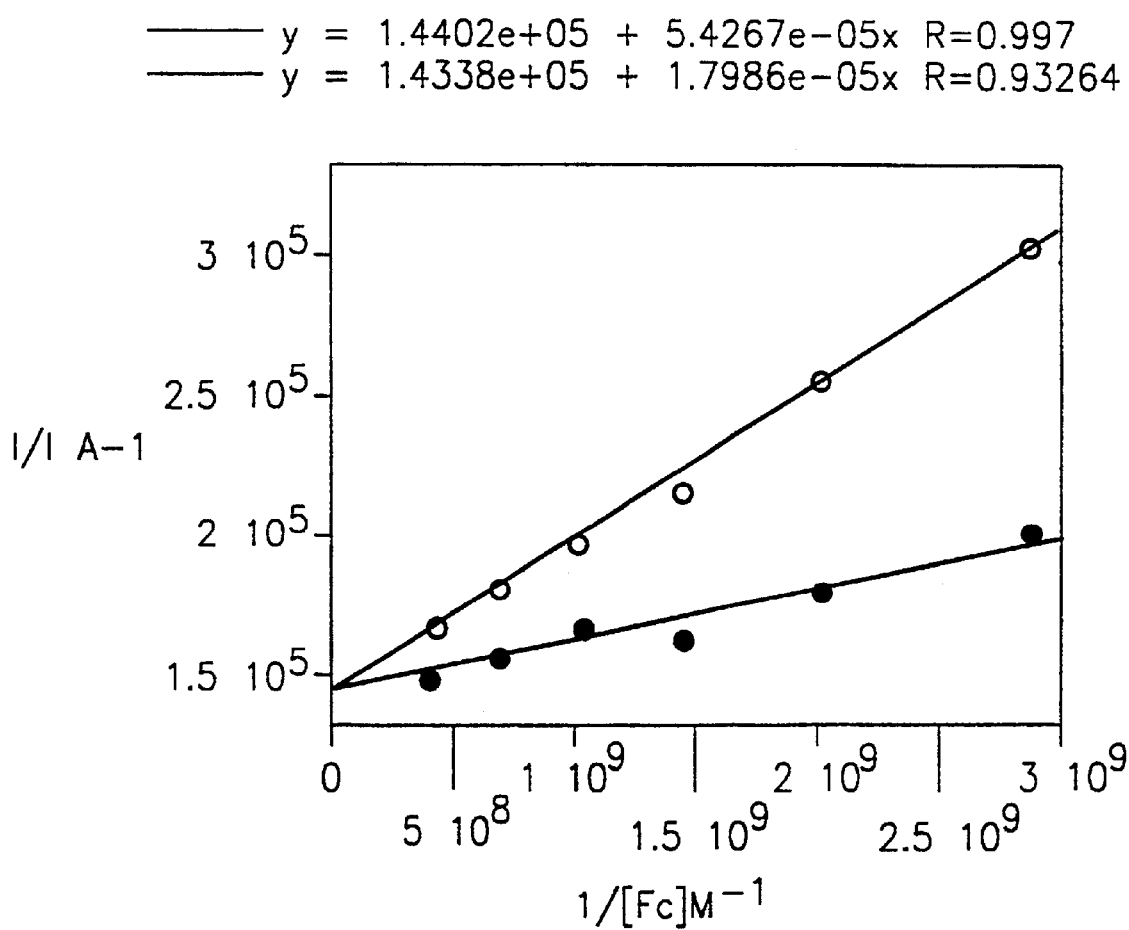
FIG. 16 shows Lineweaver-Burk plot for the saturation-current curves.

4.2 Reconstitution of Apo-Glucose Oxidase with a Nitrospiropyran-Modified FAD Cofactor Yields a Photoswitchable Biocatalyst The apo-GOD reconstituted with photoisomerizable FAD-SP diad has no direct non-mediated electrical communication with an electrode. Therefore, bioelectrocatalytic glucose oxidation using this reconstituted enzyme was studied in the presence of diffusionally mobile electron transfer mediators (ferrocene derivatives: ferrocene monocarboxylic acid, ferrocene dicarboxylic acid and dimethylaminoethyl ferrocene). The reconstituted enzyme was applied in the solubilized form or immobilized as a monolayer (see 3.3). FIG. 14 shows the cyclic voltammograms obtained upon electrobiocatalized oxidation of glucose in the presence of ferrocene carboxylic acid as a diffusional electron transfer mediator and the FAD-SP-reconstituted GOD. The electrocatalytic anodic current in the presence of the FAD-MRH$^+$ reconstituted GOD is enhanced by about 25% as compared to the FAD-SP-reconstituted GOD, implying the higher activity of the FAD-MRH$^+$-GOD. The anocid currents developed by the systems in the presence of glucose are different for both isomeric states: SP and MRH$^+$: the system is "ON" and "OFF" (FIG. 15). The detailed Michaelis-Menten kinetic analysis of the biocatalytic performances of FAD-SP-GOD and FAD-MRH$^+$-GOD in the presence of different concentrations of ferrocene carboxylic acid is shown in FIG. 16. The two photoisomer states of the enzyme reveal similar $I_{max}$=6.9·10$^{-6}$ A values, where the $K_m$ values of the two enzyme states differ substantially (7.82 M$^{-1}$ and 2.57 M$^{-1}$ for FAD-SP-GOD and FAD-MRH$^+$-GOD, respectively). These results imply that the electron transfer rate of the oxidation of the FAD cofactor by the ferrocenylium cation is of similar effectiveness in the two photoisomer states of the reconstituted GOD, but the interactions of the electron mediator with the protein to attain the appropriate configuration for electron transfer differ for both isomers. For low concentrations of the electron transfer mediators the difference in the biocatalytic activity was higher and this difference depended on the kind of the electron transfer mediator which was used. For example, the difference in the enzyme activities for SP and MRH+states was even higher if dimethylaminoethyl ferrocene was used as an electron transfer mediator (results not shown).

The FAD-SP-reconstituted GOD was assembled as a monolayer and applied for biocatalytic glucose oxidation in the presence of diffusionally mobile electron transfer mediator. The monolayer can be transformed into two different isomeric states by light (FIG. 17). FIG. 18 shows cyclic voltammograms for reversible activation and deactivation of the monolayer modified electrode for bioelectrocatalytic glucose oxidation by light. The activation (biocatalytic system comprising the reconstituted GOD and diffusional mediator is in "ON" state) and deactivation (the system is in "OFF" state) can be reversibly repeated many times (FIG. 19).

4.3 Electrical Wiring of Glucose Oxidase by Reconstitution of FAD-Modified Monolayers Assembled onto Au-Electrodes The electrode modified with the FAD component only (see 3.4) was used to reconstitute the apo-GOD directly on the interface. The immobilized FAD revealed a characteristic reversible cyclic voltammogram, $E°$ (at pH=7.0)=–0.50 V vs SCE. The interfacial electron transfer rate constant between the electrode and FAD unit was ca. 230 $s^{-1}$ and the surface concentration of the FAC units on the electrode was ca. $3·10^{-11}$ mol/$cm^2$ that corresponds to a non-densely packed monolayer coverage. However, the reconstituted GOD on the electrode did not show any biocatalytic activity in the absence of electron transfer mediators. This results from the inability of electrons to transfer between the electrode and the FAD units incorporated into the apo-protein. It should be noted that the distances between the electrode and the electrochemical centers of the FAD unity depends on the mobility of the FAD units. Free (non-incorporated into the protein) FAD units are immobilized through long flexible spacers, are mobile and can thus exchange electrons with the electrode; but the FAD units incorporated already into the protein lost this mobility, and have a long distance from the electrode surface and can thus not communicate electrically with the electrode. However, the biocatalytic activity can be achieved in the presence of diffusionally mobile electron transfer mediator (FIG. 20).

To improve the system described above, an electrode modified with two redox components: PQQ and FAD was used (see 3.5). FIG. 21 (curve a) shows the cyclic voltammogram of the PQQ-FAD diad monolayer modified electrode. It consists of two redox waves at $E°$ (at pH=7.0)=–0.125 and –0.50 V vs SCE corresponding to the two-electron reduction of the PQQ and FAD units, respectively. The surface density is ca. $3·10^{-11}$ mol cm^P2 for each component of the monolayer. The PQQ-FAD monolayer was further treated with apo-GOD to produce the reconstituted GOD directly on the modified interface. FIG. 21 (curve b) shows the cyclic voltammogram of the resulting electrode after reconstitution. The redox wave characteristic of the FAD units decreases dramatically, whereas the redox wave corresponding to the PQQ component is not changed. This is consistent with the fact that the FAD component embedded n the protein as a result of reconstitution, lacks electrical communication with the electrode surface. The small residual FAD wave observed after reconstitution corresponds to free FAD units that still communicate with the electrode. From the difference in the FAD wave before and after reconstitution the surface density of the GOD on the electrode surface was estimated to be about $1.7·10^{-12}$ mol/$cm^2$. The enzyme reconstituted onto the PQQ-FAD diad monolayer reveals direct electrical communication with the electrode and is active in the bioelectrocatalyzed oxidation of glucose. FIG. 22 shows the cyclic voltammograms of the PQQ-FAD reconstituted GOD monolayer electrode in the absence (curve a) and presence (curve b) of glucose. A high electrocatalytic anodic current is observed with glucose indicating that the reconstituted protein bioelectro-catalyzes the glucose oxidation very efficiently. The PQQ component of the monolayer functions as an electron transfer mediator between the FAD incorporated into the protein and the electrode. The electrocatalytic anodic currents developed by the system are controlled by the glucose concentration in the range 5–80 mM (FIG. 23). Dioxygen affect the electron transfer from the reconstituted GOD through PQQ to the electrode only slightly (for 80 mM glucose the anodic current decreased in the presence of oxygen only by about 5%) that is very unusual for glucose biosensors based on GOD (results not shown). Addition of 0.1 mM ascorbate (usual interfering component in vivo) to the system containing 5 mM glucose did not affect the amperometric response of the electrode. These results suggest that the reconstituted PQQ-FAD-GOD monolayer exhibits efficient electrical communication with the electrode surface that competes with the interfering paths.

4.4 Turnover Rate of GOD Reconstituted onto a PQQ-FAD Monolayer: Lack of Interference from Oxidizing and Reducing Agents The upper limit of the turnover rate of glucose oxidase at 25° C. is GOD±100 $s^{-1}$ (C. Bourdillon et al., *J. Am. Chem. Soc.*, 115:12264 (1993)) and the activation energy is 7.2 Kcal·$mole^{-1}$ (H. G. Eisenwiener, *Naturwissenschaften*, 56:563, (1969)). At the temperature employed in the electrobiochemical measurements shown in FIG. 22 and FIG. 23, (35° C.) this translates to a limiting turnover rate of 900±150 $s^{-1}$ at 35° C. The surface coverage of the reconstituted enzyme on the electrode is $1.7·10^{-2}$ and using the theoretic turnover rate at 35° C., the maximum current density that can be observed from the electrode is 290±60 $\mu A·cm^{-2}$. FIG. 23 shows that at a glucose concentration of 80 mM, the observed current is 1.9 mA (for an electrode with a surface area of 0.4 $cm^2$ and roughness factor of Ca.20). This translates to an experimental current density corresponding to 300±100 $\mu A·cm^{-2}$, a value that is within the range of the limiting turnover rate of the enzyme. This is further supported by the fact that the current response is linear with glucose concentration, FIG. 23, indicating that the S current is controlled by the diffusion of glucose to the active site and that the FAD sites exist in their oxidized form at E≈0.2 Volt.

The essentially lack of interference from surrounding redox reagents is demonstrated in FIG. 24. This is a result of the very high turnover rate of the enzyme which renders it essentially insensitive to non-specific interferences. Thus, an electrode of this kind can be used for continuous measurement in an unprotected environment, e.g. in vivo.

What is claimed is:

1. A process for preparing an electrode having FAD-dependent redox enzymes immobilized thereon, the process comprising:
    (a) preparing apo-enzymes by treating an FAD-dependent enzyme so as to remove the FAD-cofactor therefrom;
    (b) preparing a functionalized FAD by covalent binding to a binding moiety capable of chemical association with, attachment to or a chemical sorption to the surface of the electrode;
    (c) reacting the functionalized FAD with an electrode under conditions such that the modified FAD becomes immobilized onto the electrode through chemical association, attachment or sorption of the binding moiety onto the surface of the electrode;
    (d) reacting the electrode obtained in (c) with the apo-enzyme under conditions in which the apo-enzyme combines with the modified FAD to yield functional immobilized enzymes; and (e) reacting the electrode obtained in (d) with an enzyme substrate in the presence of a diffusional electron mediator.

2. A process for preparing an electrode having FAD-dependent redox enzymes immobilized thereon, the process comprising:

(a) treating an electrode to obtain a monolayer comprising an electron mediator group, the electron mediator group having a binding moiety which is capable of chemical association with, attachment to or chemical sorption to the surface of the electrode, the treatment comprising binding of the binding moiety onto the surface of the electrode;

(b) reacting the electrode obtained in (a) with an FAD such that the FAD becomes immobilized onto the electrode through chemical attachment to the electron mediator group;

(c) reacting the electrode obtained in (b) with apo-enzyme of an FAD-dependent enzyme under conditions in which the apo-enzyme combines with the FAD component of the immobilized FAD.

3. A process for preparing electrodes comprising immobilized enzymes with an associated photoisomerizable group which can change its isomerization state by exposure to light at a certain wavelength, thereby changing the rate of electrically induced catalytic activity of the enzyme, the process comprising:

(a) preparing an apo-enzyme by treating a FAD-dependent enzyme so as to remove the FAD therefrom;

(b) preparing a modified FAD by covalent binding of a group capable of attachment or binding to a photoisomerizable group;

(c) reacting the modified FAD with the photoisomerizable group to yield a photoisomerizable FAD;

(d) combining the apo-enzyme with the photoisomerizable FAD to yield a reconstituted photoisomerizable redox enzyme; and (e) providing an electrode carrying linking groups immobilized thereon and reacting the reconstituted enzymes with the electrodes such that the enzymes become covalently bound to the linking group.

4. An electrochemical system for determining the presence of an analyte liquid medium, the system comprising:

(a) an electrode carrying on its surface FAD-dependent enzymes, the enzymes being capable of catalyzing a redox reaction in which an analyte is converted into a product, the enzymes comprising a functionalized FAD having a binding moiety which is chemically associated with, attached to or chemically sorbed onto the surface of the electrode;

(b) an electron mediator group which can transfer electrons between the surface of the electrode and the FAD:

(c) an electrical circuitry for charging the electrode and measuring the electrical response.

5. A system according to claim 4, wherein the electron mediator group forms part of or is covalently bound to the functionalized FAD.

6. A system according to claim 4, wherein the electron mediator group is covalently bound to the enzyme.

7. A system according to claim 4, wherein the electron mediator group is freely tumbling in a medium surrounding the electrode.

8. A method for determining the presence of an analyte in a liquid medium the method comprising:

(a) providing a system according to claim 4, (b) introducing a sample of said liquid medium into the electrochemical cell of the system;

(c) charging the electrode and measuring the electrical response, a change in the electrical response as compared to an electrical response under the same condition in a control medium which does not comprise the analyte, indicating the presence of the analyte in the system.

9. A method according to claim 8, wherein the analyte determination is performed in vivo.

10. An electro chemical system for the recording of optical signals having a first wavelength and electrical transduction of the recorded signals, the system having an electrochemical cell comprising:

(a) an electrode carrying immobilized FAD-dependent redox enzymes, the enzyme having a functionalized FAD comprising a photoisomerizable group which changes its isomerization state from a first to a second state upon photostimulation of light of the first wavelength, a change in the isomerization state giving rise to a change in the rate of catalytic activity of the redox enzyme;

(b) an electron mediator group which can transfer electrons between the electrode and the FAD;

(c) a substrate for the catalytic activity of the enzyme; and (d) an electric circuitry for charging the electrode and measuring the electrical response.

11. A system according to claim 10, wherein the enzyme is immobilized onto the surface of the electrode through a linking group which is covalently bound to an external moiety on the surface of the enzyme.

12. A system according to claim 10 or 11, wherein the electron mediator group is freely tumbling in the medium surrounding the electrode.

13. A system according to claim 10, comprising a light switch emitting light at a second wavelength, said second wavelength photoisomerizes the photoisomerizable group from the second state to the first state.

14. A method for recordal of optical signals having a first wavelength and electrical transduction of the recorded optical signals, the method comprising:

(a) providing a system according to claim 10:

(b) exposing the electrode to a light source;

(c) charging the electrode and measuring the electrical response, changing the electrical response indicating exposure to light having said first wavelength.

* * * * *